(12) United States Patent
Waite et al.

(10) Patent No.: US 10,280,342 B2
(45) Date of Patent: May 7, 2019

(54) ADHESIVE MATERIALS AND METHODS OF MAKING AND USING THE SAME

(71) Applicant: The Regents of the University of California, Oakland, CA (US)

(72) Inventors: Herbert J. Waite, Goleta, CA (US); B. Kollbe Ahn, Goleta, CA (US); Craig J. Hawker, Santa Barbara, CA (US); Jinhwa Heo, Suwon (KR); Taegon Kang, Suwon (KR)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/908,956

(22) PCT Filed: Jul. 30, 2014

(86) PCT No.: PCT/US2014/048933
§ 371 (c)(1),
(2) Date: Jan. 29, 2016

(87) PCT Pub. No.: WO2015/017562
PCT Pub. Date: Feb. 5, 2015

(65) Prior Publication Data
US 2016/0160097 A1    Jun. 9, 2016

Related U.S. Application Data

(60) Provisional application No. 61/860,128, filed on Jul. 30, 2013.

(51) Int. Cl.
*C08F 12/24* (2006.01)
*C07C 33/30* (2006.01)
(Continued)

(52) U.S. Cl.
CPC .......... *C09J 143/04* (2013.01); *C07F 7/1804* (2013.01); *C08F 30/08* (2013.01); *C07C 33/025* (2013.01);
(Continued)

(58) Field of Classification Search
None
See application file for complete search history.

(56) References Cited

FOREIGN PATENT DOCUMENTS

JP          63012308 A  *  1/1988

OTHER PUBLICATIONS

Heo, J. et al., "Improved Performance of Protected Catecholic Polysiloxanes for Bioinspired Wet Adhesion to Surface Oxides", J. Am. Chem. Soc. 2012, 134, 20139-20145.*
(Continued)

*Primary Examiner* — Richard A Huhn
(74) *Attorney, Agent, or Firm* — Gates & Cooper LLP

(57) ABSTRACT

A compound of formula (I): can be used as a monomer for making an underwater adhesive polymer. The compound of formula (I) can be prepared using eugenol as a starting material.

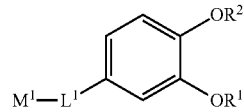

(I)

1 Claim, 15 Drawing Sheets

(51) Int. Cl.
*C09J 143/04* (2006.01)
*C07F 7/18* (2006.01)
*C08F 30/08* (2006.01)
*C08F 16/26* (2006.01)
*C09J 125/18* (2006.01)
*C09J 129/02* (2006.01)
*C07C 33/20* (2006.01)
*C07C 33/26* (2006.01)
*C07C 33/025* (2006.01)
*C07C 39/19* (2006.01)
*C07C 39/20* (2006.01)
*C08F 220/30* (2006.01)
*C09J 4/06* (2006.01)

(52) U.S. Cl.
CPC .............. *C07C 33/20* (2013.01); *C07C 33/26* (2013.01); *C07C 33/30* (2013.01); *C07C 39/19* (2013.01); *C07C 39/20* (2013.01); *C08F 12/24* (2013.01); *C08F 16/26* (2013.01); *C08F 220/30* (2013.01); *C09J 4/06* (2013.01); *C09J 125/18* (2013.01); *C09J 129/02* (2013.01)

(56) References Cited

OTHER PUBLICATIONS

Yuan, H. L. et al., "Preparation of the precursors of new tannin-like polymers with potential biological effects", Makromolekulare Chemie 1992, 193(12), 3037-3044.*

* cited by examiner

ADHESIVE MATERIALS AND METHODS OF MAKING AND USING THE SAME

CLAIM OF PRIORITY

This is a national stage application under 35 U.S.C. § 371 of PCT/US2014/048933 filed Jul. 30, 2014, the entire contents of which are incorporated herein by reference and this application claims priority to provisional U.S. Application No. 61/860,128, filed Jul. 30, 2013, which is incorporated by reference in its entirety.

STATEMENT OF GOVERNMENT SUPPORT

This invention was made with Government support under Grant No. MRSEC DMR-1121053 awarded by the National Science Foundation; Grant No. R01DE018468-05 awarded by the National Institutes of Health; Grant No. ICBWH1 by the Army Research Office, and Grant No. N000141310867 awarded by the Office of Naval Research. The Government has certain rights in this invention.

TECHNICAL FIELD

The currently claimed embodiments of this invention relate to adhesive materials and methods of making and using the same.

BACKGROUND

Adhesive proteins of marine fouling organisms (e.g., mussels, hydroids, or tubeworms) have attracted considerable interest because of their superior adhesion properties, including rapidity, strength, and versatility, under dry or wet conditions. One of the common structural elements contributing to the adhesive properties of these marine organisms is the incorporation of the catecholic amino acid 3,4-dihydroxy-L-phenylalanine (DOPA) into the adhesive proteins. Catecholic moieties in DOPA form strong coordination complexes with a host of metal ions, and can form covalent crosslinks in an oxidative environment. These moieties are thus responsible for the excellent wet adhesion properties of marine organisms.

Synthetic polymers incorporating catecholic functionalities for use as adhesives are therefore desirable. However, many synthetic challenges exist to access such artificial systems, including the difficulty in preparation of polymers including sensitive catecholic moieties. For example, unprotected catechols can irreversibly crosslink in air at neutral or basic pH, which can limit the shelf life of such materials. Furthermore, existing polymers are made from expensive starting materials. Materials and methods for making adhesive polymers having desirable adhesive properties are therefore needed.

SUMMARY

In one aspect, a monomer for making an underwater adhesive polymer includes a compound of formula (I):

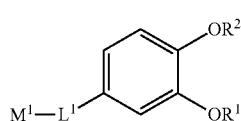

(I)

where each of $R^1$ and $R^2$, independently, can be H, alkyl, or a protecting group. $L^1$ can be a linker moiety. $M^1$ can be a polymerizable moiety. The compound of formula (I) is not eugenol, 3,4-dihydroxyphenylalanine or 3,4-dihydroxycinnamic acid.

In another aspect, a method of making an adhesive polymer includes polymerizing a monomer of formula (I) where the monomer of formula (I) is optionally polymerized with one or more additional monomers.

In another aspect, a polymer includes a repeating unit having the formula:

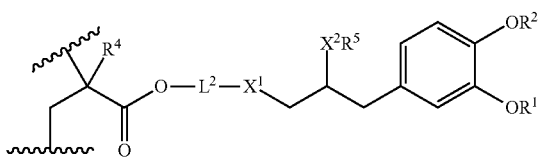

where each of $R^1$ and $R^2$, independently, can be H, alkyl, or a protecting group; $X^1$ can be a bond, O, or S; $L^2$ can be a bond, $-(CHR^a)_n-$, $-[CH_2CH(R^a)O]_n-$, or a combination thereof; each $R^a$, independently, can be H or alkyl; each n, independently, can be an integer from 1 to 10; $R^4$ can be H or $C_1$-$C_6$ alkyl; $R^5$ can be H, $C_1$-$C_6$ alkyl, or aryl; and $X^2$ can be a bond, O or S.

Other features, objects and embodiments will be apparent from the description, claims and drawings.

BRIEF DESCRIPTION OF THE DRAWINGS

FIG. 1a shows an adult mussel attached to a mica sheet by a byssus. The extended foot is making a new plaque and thread. FIG. 1b shows a schematic zoom of a foot viewed from underside, showing the distal depression lifting off from a completed plaque. The footprint denotes the distal-most part of each plaque in intimate contact with the surface. FIG. 1c schematically illustrates adhesion of DOPA-including mussel foot proteins adhered to the surface via metal-covalent and hydrogen bonds.

DETAILED DESCRIPTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without departing from the spirit and scope of the invention. All references cited herein are incorporated by reference as if each had been individually incorporated.

Figure 1:
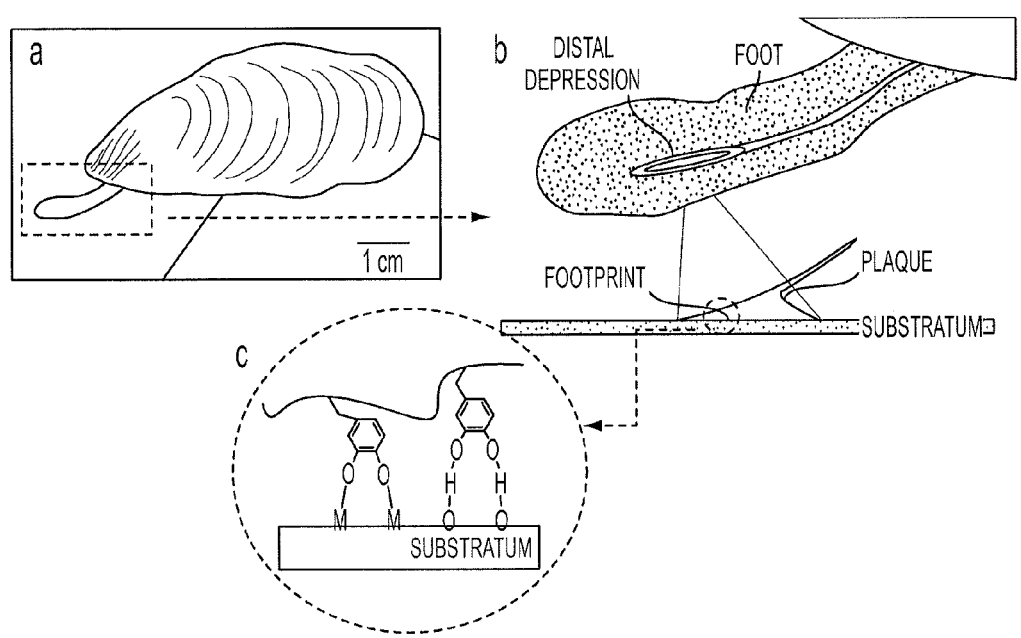
FIGS. 1a-1c illustrate byssal adhesion in the California mussel *Mytilus californianus*.

Marine organisms, for example mussels, routinely stick to a wide variety of surfaces underwater using complex fluids that spread spontaneously and exhibit strong reversible interfacial bonding and tunable cross-linking. The byssus of a California mussel (*Mytilus californianus* Conrad) resembles a bundle of threads, each of which is distally tipped by a flared adhesive plaque (FIGS. 1a-1b). Mussel adhesion is mediated by foot proteins (mfps) rich in a catecholic amino acid, 3,4-dihydroxyphenylalanine (dopa). Dopa-derived catechol moieties in the mussel plaque is the operational "wet" adhesive functionality on most polar surfaces. The catechol moieties form strong bidentate interactions, e.g., binuclear chelates on metal oxide/hydroxide surfaces and bidentate hydrogen bonding of phenolic OH groups to oxygen atom on other surfaces (e.g., mica) (FIG. 1c).

Underwater adhesives can be used, for example, in inks, paints, pressure sensitive adhesives, adhesive coatings, or other applications where prolonged adhesion of materials underwater is desired. In some embodiments, the underwater adhesive includes a polymer. The polymer can be a self-healing polymer.

All polymeric materials suffer damage in the course of their functional lifetimes. Few, if any, completely heal at damage sites. Despite recent progress in the design of self-mending polymeric materials based on crack-activated crosslinking, light, heat or other external stimuli, these remain less than perfectly healed, and, in the case of polymers in wet environments, self-healing technologies are even more limited than those engineered for dry conditions. Mussel adhesive holdfasts exhibit significant self-healing capabilities.

Some self-healing polymers are described in, for example, "Surface-initiated self-healing of polymers in aqueous media," Ahn, B. K., et al., *Nature Materials*, Advance Online Publication, Jul. 27, 2014, DOI: 10.1038/NMAT4037, which is incorporated by reference in its entirety.

Notwithstanding this, the self-mending adhesion and cohesion of isolated dopa (3,4-dihydroxyphenyl-L-alanine)-containing adhesive proteins were shown to rely critically on maintaining dopa in an acidic and reducing environment. Significantly different conditions are required to recapitulate the self-healing cohesion of tris-dopa-$Fe^{3+}$-mediated complexes in proteins and polymers. Such results increasingly suggest the importance of dopa, but also its subtle and diverse interfacial reactivity vis-à-vis the traditional and still widely held view that dopa, and catechols generally, function primarily as crosslinkers after their 2-electron oxidation to quinones.

Eugenol has a catechol moiety suitable for use in adhesive coatings, e.g., underwater adhesives and/or self-healing polymers. Desirably, eugenol is an inexpensive, renewable material derived from plant sources (e.g., clove oil), and is readily available in large quantities.

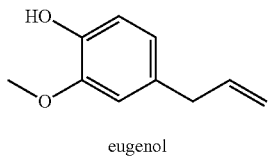

eugenol

In an embodiment, acrylic mussel-inspired adhesives derived from eugenol that possess excellent underwater tack properties are described.

As used herein, the terms "(meth)acrylate" includes both acrylate and/or methacrylate groups.

As used herein, the term "polymerizable moiety" refers to a moiety that includes a reactive functional group that can react with similar or different functional groups of one or monomers, oligomers, prepolymers, polymers, or a combination thereof, to form a polymeric product. A polymerizable moiety can be part of a monomer, oligomer, prepolymer, or polymer. The polymerizable moiety can become incorporated into a homopolymer or copolymer. Non-limiting examples of polymerizable moieties include acrylate, methacrylate, cyanoacrylate, epoxide, episulfide, styryl, vinyl, isocyanate, silicone, siloxane, and the like. Other examples of polymerizable moieties are known in the art.

As used herein, the term "monomer" refers to a discrete, non-oligomeric, non-polymeric compound which includes one or more polymerizable moieties, but does not include repeating polymerized units of the polymerizable moiety. As used herein, the term "oligomer" refers to a compound including from 2 to 10 repeating units derived from polymerization of a monomer. An oligomer optionally includes one or more polymerizable moieties (i.e., one or more polymerizable moieties that remain unreacted and capable of further polymerization). As used herein, the term "polymer" refers to a compound having more than 10 repeating units derived from polymerization of a monomer. A polymer optionally includes one or more polymerizable moieties (i.e., one or more polymerizable moieties that remain unreacted and capable of further polymerization). In some embodiments, a monomer, oligomer, or polymer can include more than one polymerizable moiety, which can be the same or different. For example, a di(meth)acrylate can include two (meth)acrylate moieties which are the same; or in another example, a compound can include an (meth)acrylate moiety and an epoxide moiety which are different.

A monomer for making an underwater adhesive polymer can include a compound of formula (I):

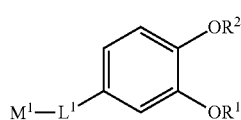

(I)

where each of $R^1$ and $R^2$, independently, can be H, alkyl, or a protecting group. $L^1$ can be a linker moiety. $M^1$ can be a polymerizable moiety. In some embodiments, the compound of formula (I) is not eugenol, 3,4-dihydroxyphenylalanine, or 3,4-dihydroxycinnamic acid.

The monomer can be a compound of formula (II):

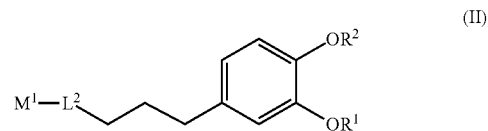

(II)

where each of $R^1$ and $R^2$, independently, can be H, alkyl, or a protecting group, provided that at least one is a protecting group. $L^2$ can be a linker moiety including a bond, —O—, —S—, —C(O)—, —C(O)NH—, —C(S)—, —[CH$_2$CH(R$^a$)O]$_n$—, or a combination thereof. Each $R^a$, independently, can be H or alkyl. Each n, independently, can be an integer from 1 to 10.

In some embodiments, $M^1$ can be an organic polymerizable moiety selected from the group consisting of an acrylate group, a methacrylate group, a cyanoacrylate group, an epoxide group, an episulfide group, a styryl group, a vinyl group, and an isocyanate group.

In some embodiments, $R^1$ and $R^2$ are not simultaneously H. In some embodiments, at least one of $R^1$ and $R^2$ is a protecting group. In some embodiments, $R^1$ is a trialkylsilyl group and $R^2$ is a trialkylsilyl group.

In some embodiments, $L^1$ does not include an —NH— or an —NHR moiety; and $M^1$ does not include an —NH— or an —NHR moiety; wherein R is a substituent.

The monomer can be a compound having the formula:

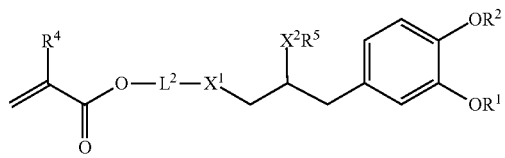

where $X^1$ can be a bond, O, or S. $L^2$ can be a bond, —(CHR$^a$)$_n$—, —[CH$_2$CH(R$^a$)O]$_n$—, or a combination thereof. $R^4$ can be H or $C_1$-$C_6$ alkyl. $R^5$ can be H, $C_1$-$C_6$ alkyl, or aryl. $X^2$ can be a bond, O or S.

In some embodiments, the compound has the formula:

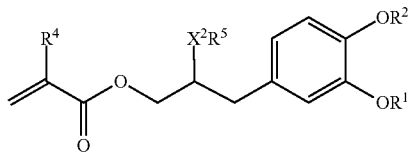

where $R^4$ is H or methyl; and $X^2$ is O or S.

The monomer can be polymerized to produce a polymer having a repeating unit having the formula:

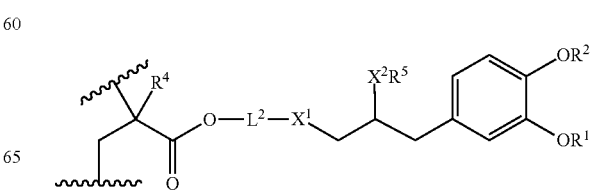

where each of $R^1$ and $R^2$, independently, is H, alkyl, or a protecting group; $X^1$ is a bond, O, or S; $L^2$ is a bond, —(CHR$^a$)$_n$—, —[CH$_2$CH(R$^a$)O]$_n$—, or a combination thereof; each $R^a$, independently, is H or alkyl; each n, independently, is an integer from 1 to 10; $R^4$ is H or $C_1$-$C_6$ alkyl; $R^5$ is H, $C_1$-$C_6$ alkyl, or aryl; and $X^2$ is a bond, O or S.

In some embodiments, the polymer includes a repeating unit having the formula:

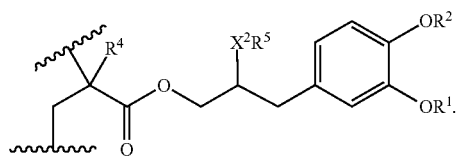

In some embodiments, the polymer is a copolymer. The copolymer can be, for example, a random or block copolymer. The copolymer can include repeating units derived from a (meth)acrylate monomer, an epoxide monomer, an episulfide monomer, a styryl monomer, a vinyl monomer, or an isocyanate monomer, or other types of monomers.

In some embodiments, a monomer is prepared using eugenol as a starting material. In general, a compound of formula (I) can be made according to the following scheme:

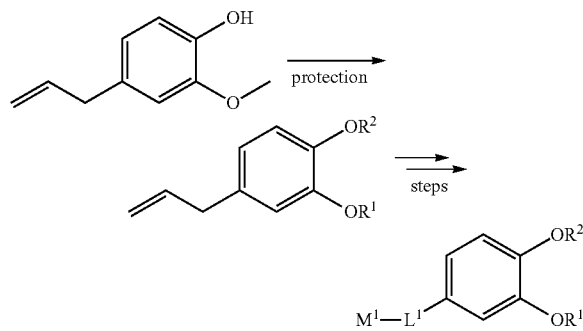

The steps to modify the protected intermediate can include, for example, modification of the allyl group, e.g., by oxidation or thiol-ene chemistry:

For example, the —OH and —OCH$_3$ groups of eugenol can be protected according to the following scheme in an illustration of one embodiment:

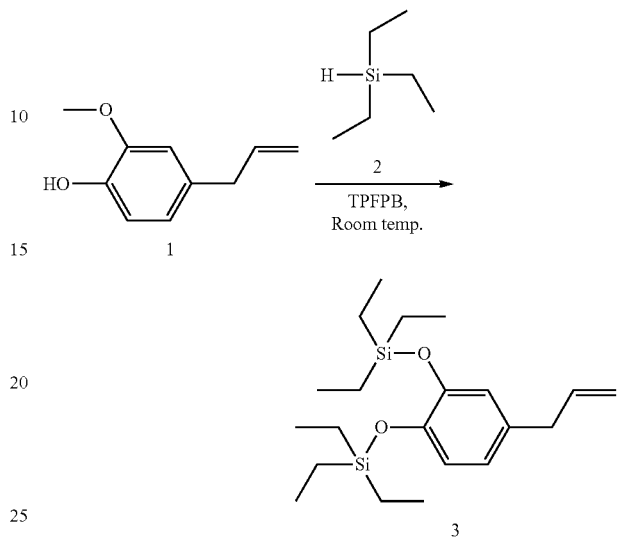

According to the scheme above, hydrosilation of both the alcohol and aryl ether of eugenol (1) was achieved in a one-pot transformation catalyzed by tris(pentafluorophenyl) borane (TPFPB) in the presence of triethylsilane (2). The reaction occurred cleanly between 1 and 2 at room temperature and under ambient conditions with complete consumption of starting materials occurring after 10 minutes. After the reaction, the silyl-protected catecholic moiety (3) was filtered through neutral alumina to remove the TPFPB, followed by evaporation to isolate 3 as a pure product in quantitative yields without the need of further purification. Conveniently, the resulting silyl-protected catecholic moiety (3) retains the alkene group that can used as a reactive handle for optional further modification, e.g., adding a polymerizable moiety.

In some embodiments, a compound of formula (I) can be made from eugenol according to the following scheme:

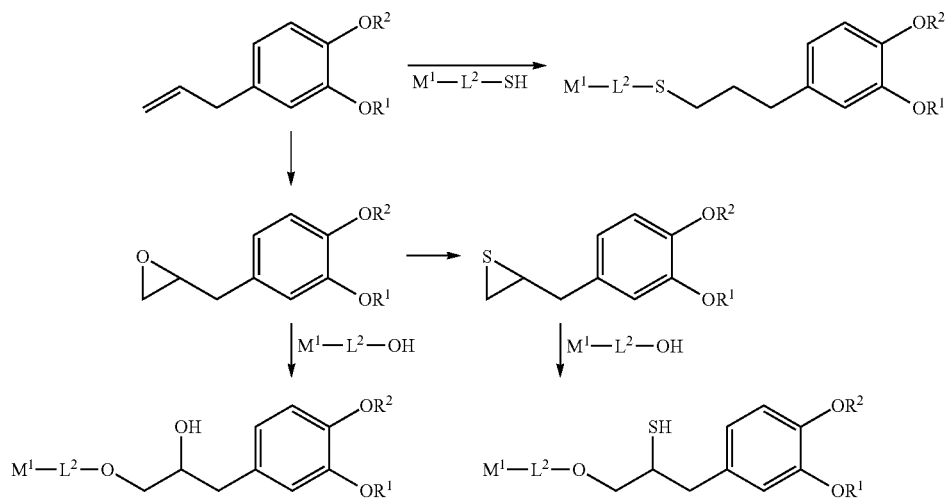

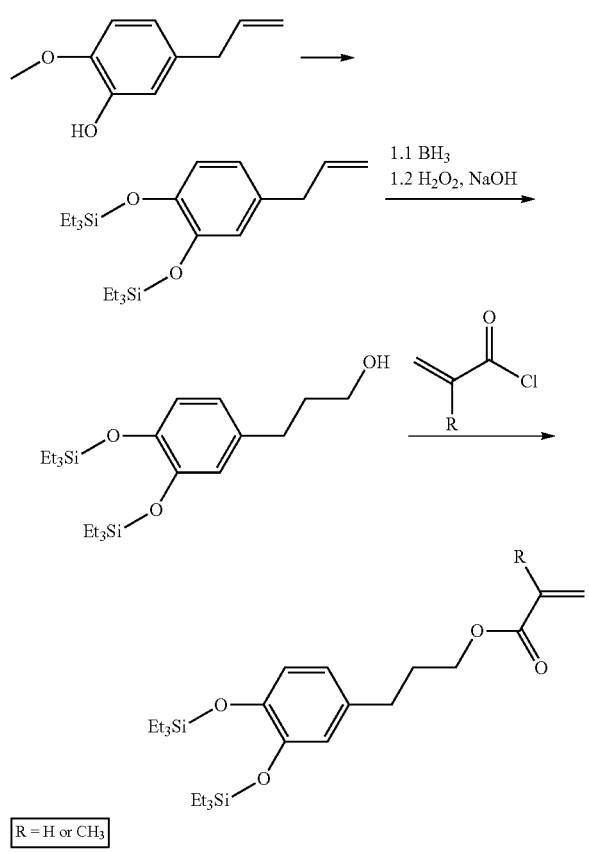

In some embodiments, the alkene group (of eugenol) itself can act as a polymerizable moiety. See, for example, Heo, J.; Kang, T.; Jang, S. G.; Hwang, D. S.; Spruell, J. M.; Killops, K. L.; Waite, J. H.; Hawker, C. J.; "Improved Performance of Protected Catecholic Polysiloxanes for Bio-inspired Wet Adhesion to Surface Oxides," *J Am. Chem. Soc.* 2012, 134, 20139-20145, which is incorporated by reference in its entirety.

Figure 4:
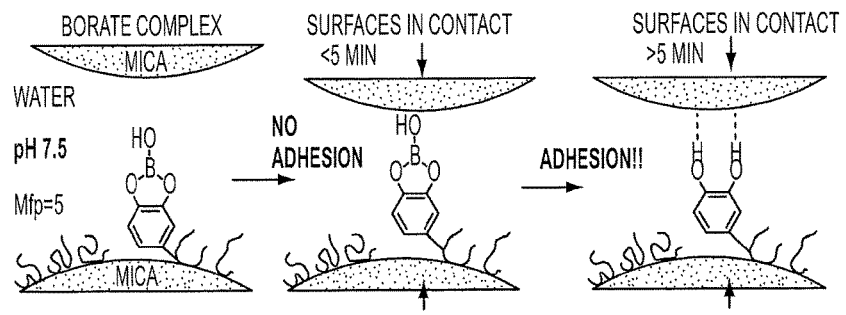
FIG. 4 schematically illustrates adhesion of borate-protected catechol polymers between mica surfaces.

The protecting groups can preserve the catechol moiety during and after modification of eugenol, e.g., installing a polymerizable moiety. Because the catechol moiety is protected, the monomers can have good shelf life. A variety of catechol protecting groups, including silyl and borate protecting groups, are available. The stability of the catechol moiety to oxidation can be controlled by choice of the protecting group. The protecting group chosen also affects the efficiency of the protection and deprotection reactions, and the conditions needed for carrying out those reactions. For example, triethyl silyl protecting groups can be conveniently removed in pH 3 acetic acid buffer solution. Silyl protecting groups can also be removed using other reagents, e.g., tetra-n-butylammonium fluoride. Silyl ethers can be made with a range of stability toward acid deprotection, e.g., trimethylsilyl<triethylsilyl<tert-butyldimethylsilyl<tert-butoxydiphenylsilyl. However, more stable protection requires harsher conditions for deprotection. Borate-protected catechol moieties can conveniently deprotected under mild conditions, e.g., at pH 7.5 when in contact with a mica surface (see, e.g., FIG. 4).

Figure 2A:
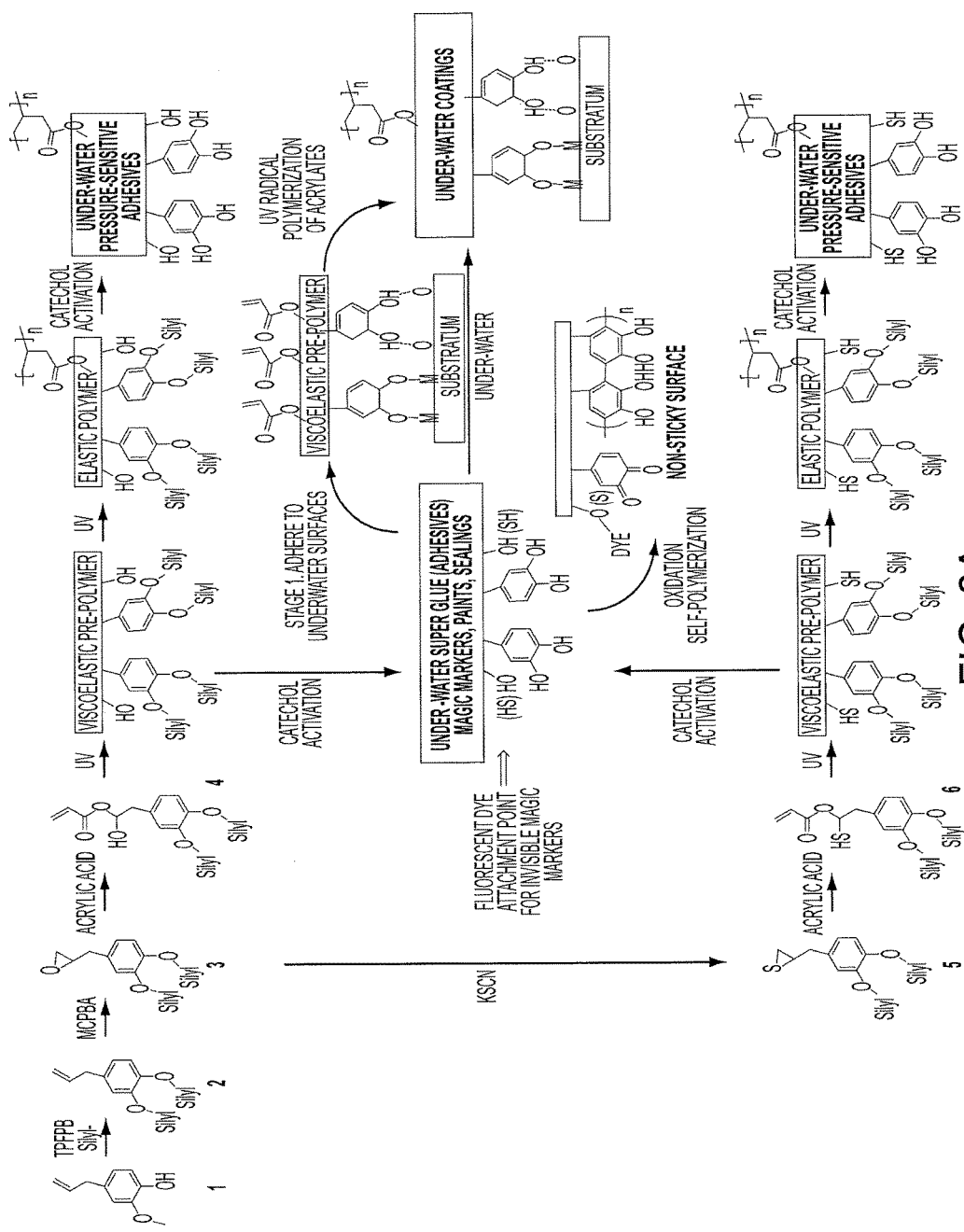
FIG. 2A is a synthetic scheme of illustrating the preparation of under-water adhesives/coatings.

Some examples of further modifications to add a polymerizable moiety are illustrated in FIG. 2A. In FIG. 2A, the allyl group of a protected eugenol is oxidized to provide an oxirane moiety, which is the subject of further modification. In one example, the oxirane undergoes reaction with a (meth)acrylic acid, to provide a monomer according to formula (I) (see compound 4 in FIG. 2A). In another example, the oxirane undergoes reaction with KSCN to provide a thiirane moiety, which is the subject of further modification, e.g., by reaction with a (meth)acrylic acid, to provide a monomer according to formula (I) (see compound 6 in FIG. 2A).

In some embodiments, the monomer of formula (I) can be partially polymerized to form a pre-polymer. In some embodiments, no other monomers are added to the monomer of formula (I) before forming a pre-polymer. In other embodiments, the monomer is combined with one or more other monomers prior to forming a pre-polymer. Once the pre-polymer has been formed, one or more additional monomers can optionally be added to the pre-polymer. In some embodiments, the pre-polymer can be applied to a substrate. In other embodiments, the monomer of formula (I) can be applied to a substrate prior to forming the pre-polymer. In some embodiments, the pre-polymer can be a viscoelastic pre-polymer. A viscoelastic pre-polymer in some embodiments be desirable for application to a substrate.

In some embodiments, the pre-polymer can be further polymerized to provide a final polymer. In some embodiments, the final polymer can be an elastic polymer; for example, the pre-polymer can be a viscoelastic pre-polymer and the final polymer can be an elastic polymer. Additional polymerization steps may be carried out if desired.

In some embodiments, a pre-polymer is not formed prior to forming a final polymer. In such a case, the monomer of formula (I) can optionally be combined with one or more additional polymers and subjected to a single polymerization step to produce a final polymer.

Deprotection (in other words, activation of the catechol groups) can be carried out at any stage, e.g., prior to polymerization, or after one or more steps of polymerization.

The final polymer can be in the form of a coating on a substrate. The final polymer can be an adhesive, e.g., an underwater adhesive. In some embodiments, adhesive and/or cohesive properties can be modified (e.g., enhanced) upon deprotection. As discussed above, deprotection can be carried out at any stage.

In an embodiment, the monomer includes a (meth)acrylic moiety. Polymerization can be initiated by exposure to light (e.g., UV light) in the presence of a photoinitiator.

Physical properties of the adhesives can be adjusted by factors including the structure of the monomer, the degree of polymerization, the structure of any copolymers used, and the ratio of components used in forming the polymer. For example, a (meth)acrylic monomer can provide a harder final polymer than a corresponding acrylic monomer, because it produces thicker polymer chains and prevents their sliding past one another. The adhesion/cohesion balance can be adjusted by controlling the degree of polymerization and/or degree of oxidation (self-polymerization) of the catechol moieties. Adhesion refers to the strength of the interaction of the polymer with an underlying substrate, whereas cohesion refers to the strength of the polymer's self-interaction. In some embodiments, polymers disclosed herein provide a desirable level of adhesion and/or a desirable level of cohesion, particularly when used as an underwater adhesive.

EXAMPLES

Figure 2B:
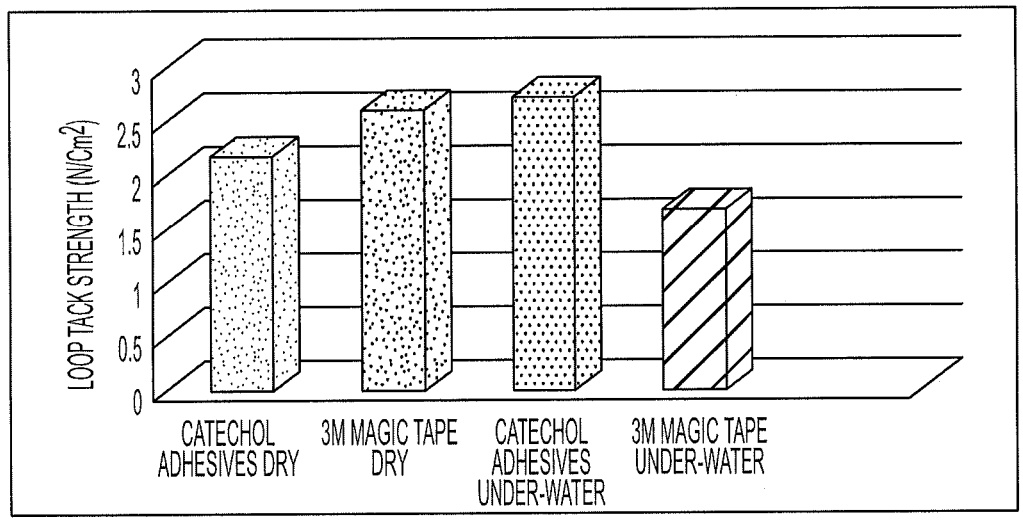
FIG. 2B is a graph depicting tack properties of the catechol-functionalized acrylic tape (PSA) vs. commercial acrylic scotch tape (3M, St. Paul, Minn.) on a steel substrate.

Acrylic-containing adhesives derived from eugenol were prepared (FIG. 2A) and demonstrated excellent under-water tack properties (FIG. 2B). The catechol acrylic pressure-sensitive adhesives (PSA:tape) and Scotch Magic tape (3M, St. Paul, Minn.) were attached to steel and removed under both dry and underwater conditions. For underwater conditions, tapes were soaked in water for 30 seconds, then attached and removed under water. The Scotch tape possessed higher tack strength at 2.5 N/cm$^2$ than catechol tape at 2.2 N/cm$^2$ under dry conditions, Underwater, the tack strength of the catechol tape at 2.6 N/cm$^2$ was greater than that of the Scotch tape 1.6 N/cm$^2$. The underwater tack strength of the catechol tape was even stronger than the dry tack of Scotch tape.

Figure 3:
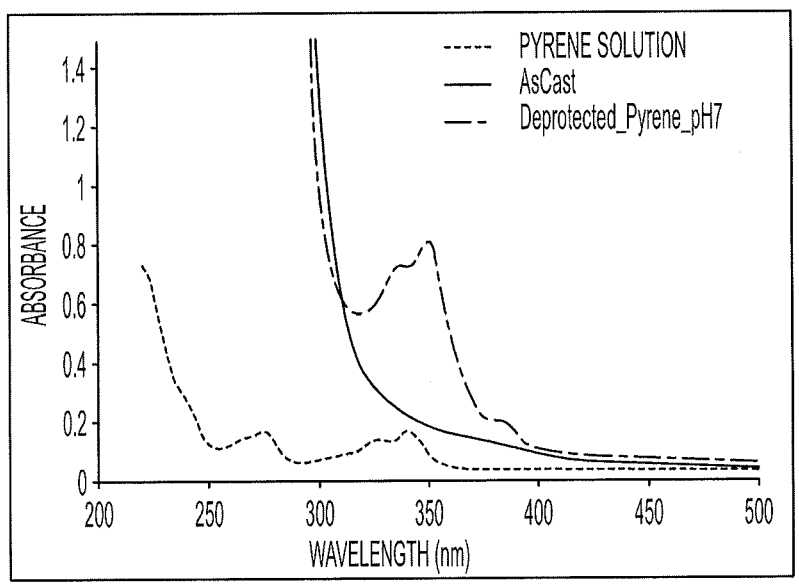
FIG. 3 shows the UV spectra of poly(eugenol acrylates) (PEA) as cast (red line), pyrene-dyed catechol deprotected PEA (blue), and pyrene dye (green).

A dye binding study was used to determine the presence of catechol units in the film after aqueous deprotection of the UV-cured poly(eugenol acrylates) films Monomers were drop-cast and UV cured on quartz slides. These slides were then incubated in pH 3 acetic acid buffer for 1 hour to promote silane deprotection. The deprotected slides were soaked in a 0.5 mM pyrene-1-boronic acid solution in a 50/50 mixture of pH 7.4 PBS/methanol expected to yield catechol-boronate complexation. UV-vis spectra showed the presence of the pyrene chromophore as evidence of existing catechol moieties after incubation and extensive washing with buffer solution (FIG. 3).

Final physical properties of the adhesives/coatings are modulated by replacing acrylic acid with methacrylic acid in the reaction from 3 (or 5) to 4 (or 6) (FIG. 2A) produces a poly(methacrylate) backbone instead of poly(acrylate). The addition of methyl groups on the backbone carbon chain provides stiffness (hardness) because it produces thicker polymer chains and prevents their sliding past one another.

Figure 5:
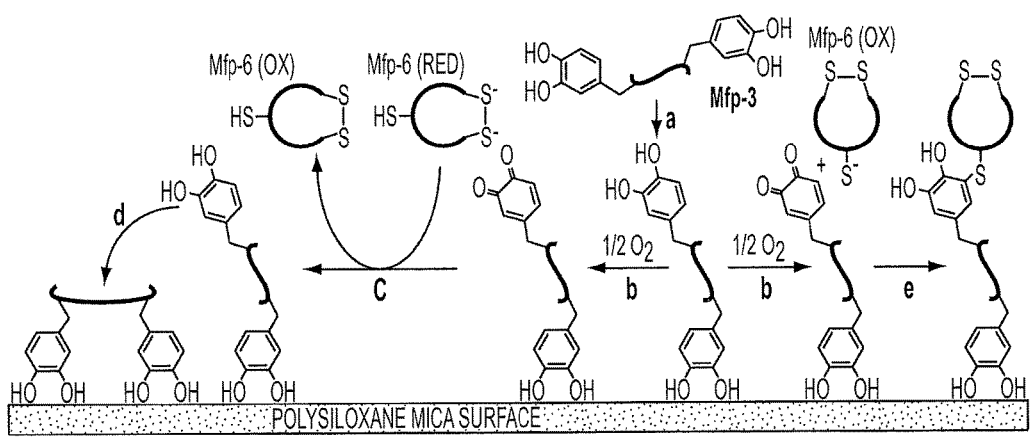
FIG. 5 schematically illustrates redox control and the stepwise adsorption and cross-linking of mfp-3. (a-e) Mfp-3 variants are secreted into the distal depression (a) and partially adsorbed by dopa mediated H-bonds to the mica surface. The oxidation of unadsorbed dopa to dopa-quinone (b) is counteracted by reducing thiolates (c) in mfp-6, which enables enhanced adsorption (d). Depletion of thiolate pairs in mfp-6 transforms mfp-6 into a cross-linker with mfp-3 (e). red, reduced; ox, oxidized.

Mussel foot protein-3 has antioxidant thiols (FIG. 5) that provide reducing equivalents to regenerate Dopa from auto-oxidation products such as quinones that exhibit weaker adhesion on mineral surfaces; the antioxidant protection appears to be transient to enable maximal surface binding by Dopa, which once bound in bidentate mode, is very slow to debond. To maintain the adhesive strength of the catechol, thiol-functionalization is applied by converting oxirane (epoxide) to thiirane (episulfide) (see FIG. 2A), analogues of the thiol-rich mussel foot proteins (mfp-6) which serves as an antioxidant to preserve catecholic functionality until surface binding.

The viscoelasticity of the pre-polymer is modulated to optimize adhesive and cohesive strength for each application by adjusting UV dose, energy, exposure time, and amount and type of photoinitiators. A flowable prepolymer can be prepared, followed by catechol activation to produce an underwater adhesive. The viscosity is adjusted along with contact angle analysis for each demand. To achieve a surface hardness for underwater coatings, additional UV exposure is applied for further radical polymerization of remaining polymerizable moieties in the prepolymer. That is, the catechol moieties in the prepolymer adhere to applied underwater surfaces (stage 1), followed by the second UV exposure, which leads the unreacted acrylic sites in the prepolymer matrix to further polymerization (stage 2).

Mechanical properties of the catechol-functionalized adhesives/coatings are investigated and characterized using the Surface Forces Apparatus (SFA) correlated to their chemical scaffolds and contents of functional groups. SFA is a technique that can distinguish between the adhesive and cohesive forces contributing to the load-bearing performance of adhesives. SFA reveals the force-distance profiles and adhesion/cohesion energies as a function of catechol contents and/or OH— and SH— contents in the polymeric matrix (Anderson, T. H. et al. The Contribution of DOPA to Substrate-Peptide Adhesion and Internal Cohesion of Mussel-Inspired Synthetic Peptide Films *Advanced Functional Materials* 20, 4196-4205, doi:10.1002/adfm.201000932 (2010)).

Once the catechol in the mussel foot protein binds in a bidentate manner to surface-bound O-atoms, it is stabilized and not oxidized so as to maintain the adhered status. This surface phenomenon is studied with SFA to investigate how super strong force necessary to break the metal-complexation to debond the under-water super glue (adhesives or sealings). In addition, fluorescent microscopy and UV spectroscopy monitors the degree of surface catechol contents. Based on surface physics investigations with the SFA, conditions are optimized for desirable mechanical properties for each application. Adhesion and cohesion to various polar and non-polar solid surfaces related to degree of polymerization and catechol/-OH/-SH contents are investigated. The loop tack, peel, shear strength tests are conducted under seawater as well as underwater based on methods described in ASTM D6195-03, D3330/D3330M-04, D3654/3654M-06, D1002, D3163, and D5868, each of which is incorporated by reference in its entirety.

Figure 6A:
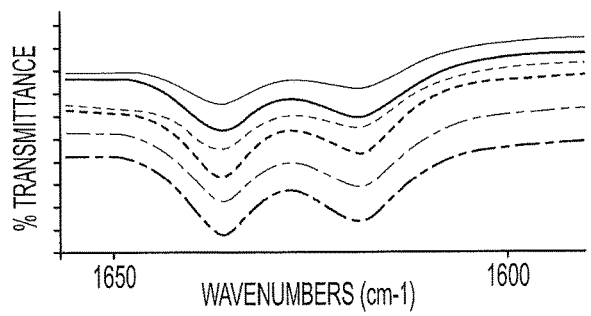
FIG. 6A shows FTIR spectra of UV-scanned acrylic resin from UV dose (bottom to top) from 645 (4 UV scans) to 1935 mJ/cm² (9 UV scans).
Figure 6B:
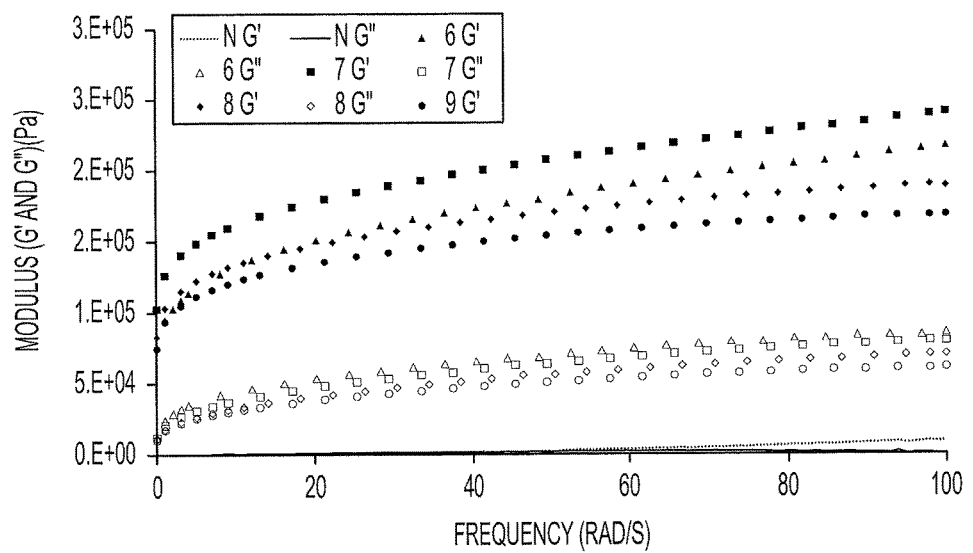
FIG. 6B shows G' and G" as a function of frequency (rad/s) of 6-9 UV scans.

The hydroxyl sites (in green in FIG. 2A) next to (meth) acrylates provide a functional handle in this system. The pre-polymerization will provide adjustable degrees of polymerization. The degree of polymerization is related to the viscosity of the pre-polymer, and different applications may benefit from different levels of viscosity; for example, a higher viscosity can be preferable for underwater marker and paint applications. The degree of (meth)acrylate polymerization was conveniently modulated by adjusting UV irradiation intensity with the Fusion UV system equipped with 300 watt/inch microwave-powered lamp and conveyor belt. See, e.g., Ahn, B. K. et al. UV-Curable, High-Shear Pressure-Sensitive Adhesives Derived from Acrylated Epoxidized Soybean Oil. *Journal of Adhesion* 89, 323-338, (2013), which is incorporated by reference in its entirety. The kinetic profiles of the UV radical polymerization of acrylates was monitored by FTIR absorbance bands at 1600 cm$^{-1}$ (C=C) as a function of increasing UV dose in proportion to the number of UV scans, and the rheological behavior (viscoelasticity) was also dependent on UV irradiation (FIGS. 6A-6B). The viscoelasticity of the prepolymer is modulated to optimize adhesive and cohesive strength for each application by adjusting UV dose, energy, exposure time, and amount and type of photo initiators. Flowable prepolymer is prepared, followed by catechol activation to produce underwater markers, paints, and glues. Viscosity is studied with rheological and contact angle analyses.

Non-sticky surfaces of magic markers, paints, and sealings can be derived from the quinone moieties formed during natural oxidation or UV oxidation. Poly(catechols) can also be generated from partial oxidation, followed by self-polymerization via aryl-aryl carbon-to-carbon coupling (FIG. 2A). A preliminary study showed evidence of a loss of tackiness on surface of the catechol-functionalized PSAs after long air/water exposures to become scratch-free coatings.

To achieve a surface hardness quickly for underwater coatings, additional UV exposure can be applied for further radical polymerization of the residue of acrylates in the prepolymer. That is, the monomer (e.g., protected monomer) is exposed to UV light to induce a partial polymerization, forming a pre-polymer. The catechol moieties in the pre-polymer adhere to applied underwater surfaces (stage 1, FIG. 2A), followed by a second UV exposure, which leads unreacted acrylic sites in the pre-polymer to further polymerization (stage 2, FIG. 2A). Mechanical properties of the coatings, such as hardness and extensibility (which is correlated to polymerization degree and catechol activation) can be controlled by selection of polymer components and polymerization conditions.

REFERENCES

Each of the following references is hereby incorporated by reference in its entirety.
1) Heo, J.; Kang, T.; Jang, S. G.; Hwang, D. S.; Spruell, J. M.; Killops, K. L.; Waite, J. H.; Hawker, C. J.; "Improved Performance of Protected Catecholic Polysiloxanes for Bioinspired Wet Adhesion to Surface Oxides," *J Am. Chem. Soc.* 2012, 134, 20139-20145
2) Wei, W., Yu, J., Broomell, C. C., Israelachvili, J. N., Waite, J. H. (2013). Hydrophobic enhancement of Dopa mediated adhesion in a muusel foot protein. *JACS* 135, 377-383.
3) J. Yu, E. Danner, R. K. Ashley, Israelachvili, and Waite, J. H. (2011). Mussel protein adhesion depends on interprotein thiol-mediated redox modulation. *Nature Chemical Biology* 7, 588-590.
4) Lee, B. P., Messersmith, P. B., Israelachvili, J. N., Waite, J. H. (2011) Mussel inspired wet adhesives and coatings. *Annual Review of Materials Research* 41, 99-132.
5) Waite, J. H. Surface chemistry—Mussel power. *Nature Materials.* 7, 8-9
6) Harrington, M. J., Masic, A., Holten-Andersen, N., Waite, J. H., and Fratzl, P. (2010). Ironclad fibers: a metal-based biological strategy for hard flexible coatings. *Science* 328, 216-220.
7) Nicklisch, S. C. T., and Waite, J. H. (2012). Role of redox in Dopa-mediated marine adhesion. *Biofouling* 28, 865-877.
8) Yu, J. Wei, W. Danner, E. Israelachvili, J. and Waite, J. H. (2011). Effects of interfacial redox in mussel adhesive protein films on mica. *Advanced Materials* 23, 2362-2366. PMC 3221558
9) Miserez, A., Wasko, S. S., Carpenter, C. F., & Waite, J. H. (2009). Non-entropic and reversible long range deformation of an encapsulating bioelastomer. *Nature Materials* 8: 910-916.
10) Holten-Andersen, N., Fantner, G. E., Hohlbauch, S., Waite, J. H., & Zok, F. W. (2007). Protective coatings on extensible biofibers. *Nature Materials* 6: 669-672
11) Danner, E. W., Kan, Y. J., Hammer, M. U., Israelachvili, J. N. & Waite, J. H. (2012). Adhesion of Mussel Foot Protein Mefp-5 to Mica: An Underwater Superglue. *Biochemistry* 51, 6511-6518
12) Matos-Perez, C. R., White, J. D. & Wilker, J. J. Polymer Composition and Substrate Influences on the Adhesive Bonding of a Biomimetic, Cross-Linking Polymer. *J. Am. Chem. Soc.* 134, 9498-9505, doi:10.1021/ja303369p (2012).

ADDITIONAL EXAMPLES

One strategy involves the preparation of DOPA functionalized polyorganosiloxanes (alternatively referred to as silicones or polysiloxanes) to serve as a generally applicable and crosslinkable artificial adhesive. See, for example, Heo, J.; Kang, T.; Jang, S. G.; Hwang, D. S.; Spruell, J. M.; Killops, K. L.; Waite, J. H.; Hawker, C. J.; "Improved Performance of Protected Catecholic Polysiloxanes for Bioinspired Wet Adhesion to Surface Oxides," *J Am. Chem. Soc.* 2012, 134, 20139-20145, which is incorporated by reference in its entirety. Silicones as a general class of materials are ubiquitous in our lives, with applications ranging widely from electrical materials to biomaterials as a result of their unique properties such as low glass transition temperature, low surface energy, transparency, good thermal and oxidative stability, low modulus, high flexibility and excellent moldability.[6-11] While polysiloxanes are capable of molding and patterning as crosslinked microstructures, the inherently low mechanical and anti-adhesive properties, as well as side reactions that could occur during traditional thermal curing processes pose complications for employing it as a catechol-based wet adhesive materials. Lee and co-workers reported polysiloxane structural pillars having wet/dry adhesiveness caused by coating an adhesive polymer onto pre-fabricated polysiloxane pillars inspired by gecko and mussels[12] biological nanostructures. While this method forms polysiloxane arrays being useful for a reversible wet/dry adhesive, it requires a costly and complicated process to both form the nanostructured polysiloxanes through electron-beam lithography and then coat these structures with under-water adhesive polymers. Of particular note is the care that must be taken to maintain the adhesive properties before application of the adhesive due to oxidative degradation of the catecholic moieties.

Our strategy overcomes these issues by employing two powerful, efficient and orthogonal reactions to prepare adhesive catechol functionalized polysiloxanes: (1) tris(pentafluorophenyl)borane (TPFPB)-catalyzed silation and (2) thiol-ene coupling. Our new class of marine-inspired adhesive polysiloxanes is thus easily synthesized in a cost effectiveness and scalable manner to provide stable materials that can be activated through a simple protecting/deprotecting process. The first enabler to our strategy, the TPFPB-catalyzed silation, has been used for hydrosilation of alcohols[13] alkoxysilanes[14-16], olefins[17], imines[18,19], enones and silyl enol ethers[20], cleavage of aryl and alkyl ethers, and reduction of alcohols[21]. This mild reaction is highly efficient and insensitive to moisture.[22-24] Moreover, the versatile reactivity of the TPFPB enables the one-pot transformation of aryl ethers into silyl protected functionalities. It is this interesting reactivity that enables the facile transformation of eugenol, a naturally occurring compound which is readily available in large quantities, into a silyl-protected DOPA mimic cleanly and in one step. The silyl protecting groups are key to maintaining these important functional groups throughout the thiol-ene polymer functionalization and crosslinking reactions. Moreover, these silyl protecting groups serve to provide long shelf-life to the assembled materials but can be selectively deprotected under acidic or basic conditions such as conventional contact printing methods, essentially activating the adhesive properties just prior to use. The second enabler is the thiol-ene reaction that allows the attachment of the critical protected eugenol moieties to the polymer backbone. This valuable reaction proceeds in high yields with tolerance for various functional groups even under solvent-free conditions and has been widely used for the modification of polymers[25-30], thin-film fabrication[31] and dendrimer synthesis[25,32,33]. Due to its high efficiency, simplicity, and quantitative control of functional group, thiol-ene reaction is an ideal partner for the quantitative functionalization of polymer and preparation of crosslinked thin films[34].

Herein, synthetic bio-inspired polysiloxanes with catechol functional groups are described. They can be prepared through facile and efficient chemistry and their adhesiveness tuned with high moldability with lack of oxidation of catechols.

The inspection of the marine organisms yields insights into a design of underwater adhesive synthetic materials. First of all, the synthetic materials should have unoxidized catecholic moieties for the adhesion properties and the concentration of catecholic moieties should be controlled to mimic the various adhesive proteins of marine organisms.

Second, highly moldable materials are desired for the fabrication of adhesive surface and the construction of 3-dimensional structures. Third, the minimal water diffusivity after application of the adhesive is expected for the robustness of the molded structures under water. Fourth, cost effective synthetic routes are required for the various applications. Finally, facile protection and deprotection methods are desired to prevent the oxidation of catecholic moieties during the synthesis and storage of the artificial adhesive materials. Catecholic moieties are easily oxidized during the polymer synthesis and processing in oxidative environment, thereby significantly reducing the adhesive properties of catechol containing polymer analog. In other words, when catechol moieties oxidize to o-quinone, they react with the other functionalities in the polymer (e.g., amine, thiols and catechols themselves) and cause extensive cross-linking and aggregation even before their intended application. Thus, we synthesized silyl-protected catechol (SPC) functionalized polysiloxane, employing eugenol as a naturally derived and economical viable precursor to protected catechol[35].

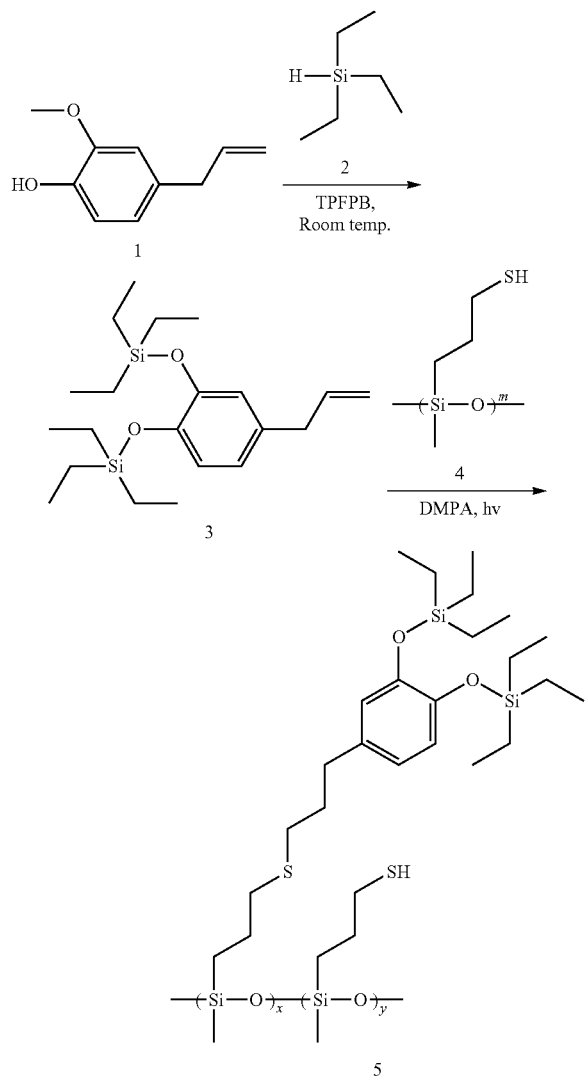

The synthetic strategy of silyl-protected catecholic moiety (3) and SPC-functionalized polysiloxane (5) is illustrated in Scheme 1. Hydrosilation of both the alcohol and aryl ether of eugenol (1) was achieved in a one-pot transformation catalyzed by tris(pentafluorophenyl)borane (TPFPB) in the presence of triethylsilane (2). The reaction occurred cleanly between 1 and 2 at room temperature and under ambient conditions with complete consumption of starting materials occurring after 10 minutes. After the reaction, the silyl-protected catecholic moiety (3) was filtered through neutral alumina to remove the TPFPB, followed by evaporation to isolate 3 as a pure product in quantitative yields without the need of further purification. Conveniently, the resulting silyl-protected catecholic moiety (3) retains the alkene group that is used as a reactive handle through which it may be appended upon a polymer backbone. Employing commercially available poly[(mercaptopropyl)methylsiloxane] (PMMS) (FIG. 7a) as the thiol-functional siloxane precursor, polymers functionalized with protected catechol were easily prepared with varying incorporations (5-50 mol %) of the adhesive catechol-analog along the backbone through the thiol-ene reaction. Photoirradiation at 365 nm of a neat mixture of the polymer (4), silyl-protected catecholic moiety (3), and 2,2-dimethoxy-2-phenylacetophenone (DMPA) as a photoinitiator for 30 minutes resulted in the clean incorporation of the protected catechol. The percent incorporation was controlled simply through the feed ratio of the ene to thiol groups within the mixture (FIG. 7b), where the actual incorporation matched the feed ratio.

Figure 7:
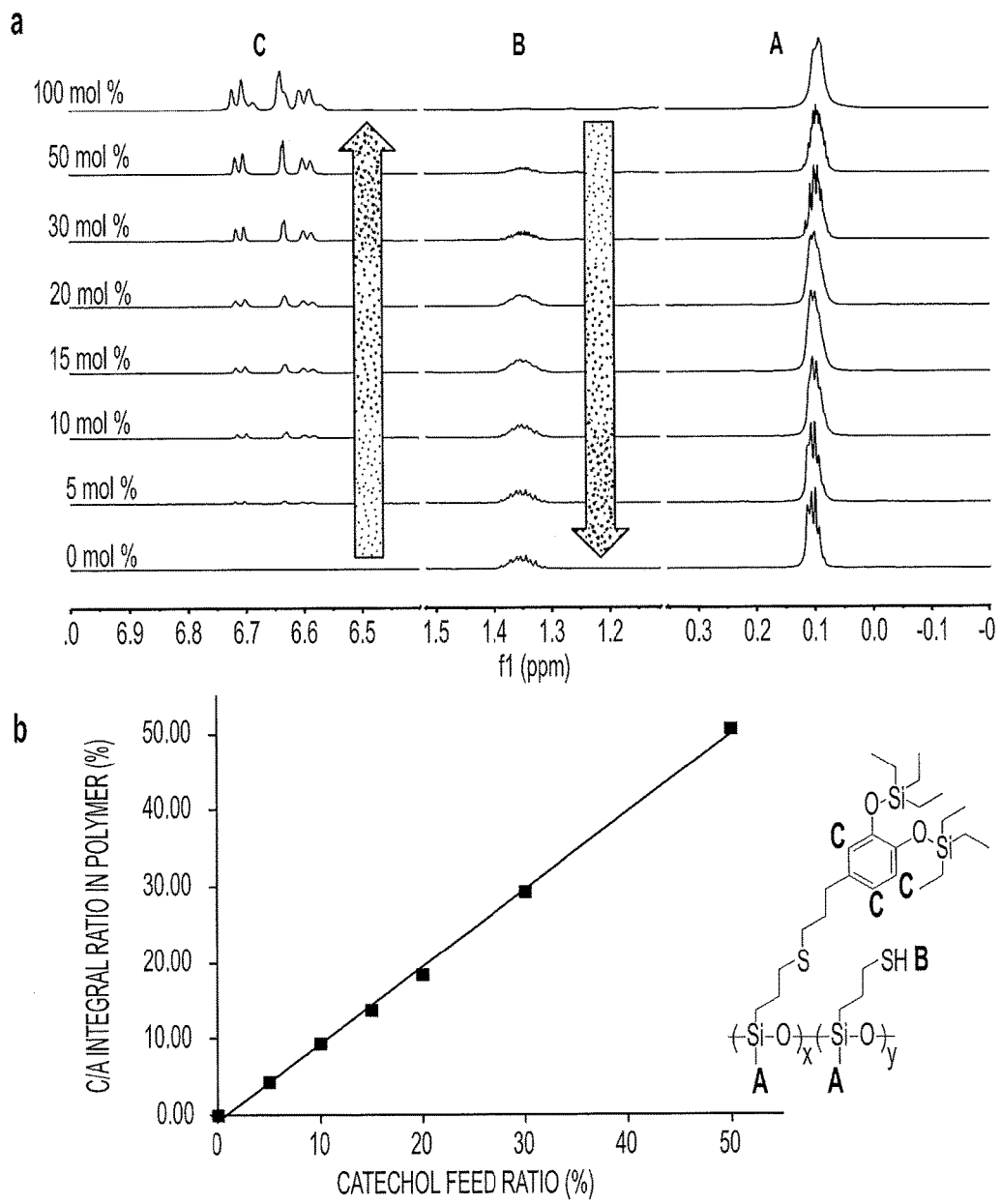
FIG. 7 (a) $^1$H-NMR spectra of SPC-functionalized polysiloxane with different ratio of silyl-protected catecholic moiety. All spectra are normalized to the intensity of the methyl resonance near 0.1 ppm (b) catechol/methyl (C/A) ratio of integral values of $^1$H-NMR spectra versus catechol feed ratio.

FIG. 7a displays the $^1$H-NMR spectra of various SPC-functionalized polysiloxanes prepared in this manner where the incorporation of the ene-moieties is easily determined. The relative integrated intensity of the signals corresponding to the methyl groups occurring at every repeat unit as compared to those occurring from the aryl groups of the catechol allows the calculation of the percent incorporation of the silyl-protected catecholic moieties as a function of the feed ratio. While we functionalized the thiols with catecholic moieties up to 100 mol %, the highest loading we used for this study was 50 mol %. For comparison sake, the highest DOPA loading in nature occurs in the mussel foot protein-5 (mfp-5) with roughly ~30 mol % loading in mussels belonging to the *Mytilus* genus. Our polymers are therefore good analogs of those employed by these amazing marine creatures, furthermore, no other reports have been made for the production of polymers bearing such high loadings of catecholic moieties. Of final note, it should be emphasized that the silyl protecting groups remain in place throughout the thiol-ene functionalization, as indicated by the signal at 0.98 and 0.74 ppm in the $^1$H-NMR spectra. The presence of these groups insures that the catechol groups will (1) not take place in any unwanted adhesion and (2) will not degrade through oxidative pathways.

Figure 8:
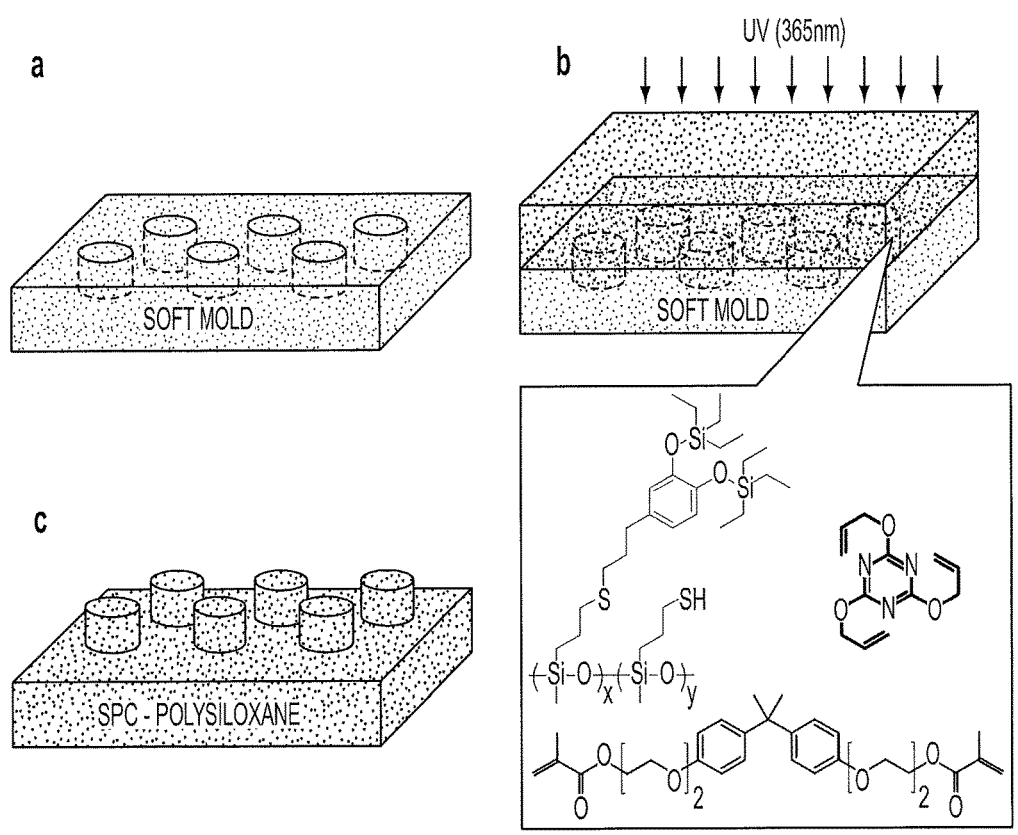
FIG. 8 (a) preparation of soft mold, (b) casting mixture of SPC-functionalized polysiloxane onto patterned soft mold and photocuring and (c) replica mold with SPC-functionalized polysiloxane.
Figure 9:
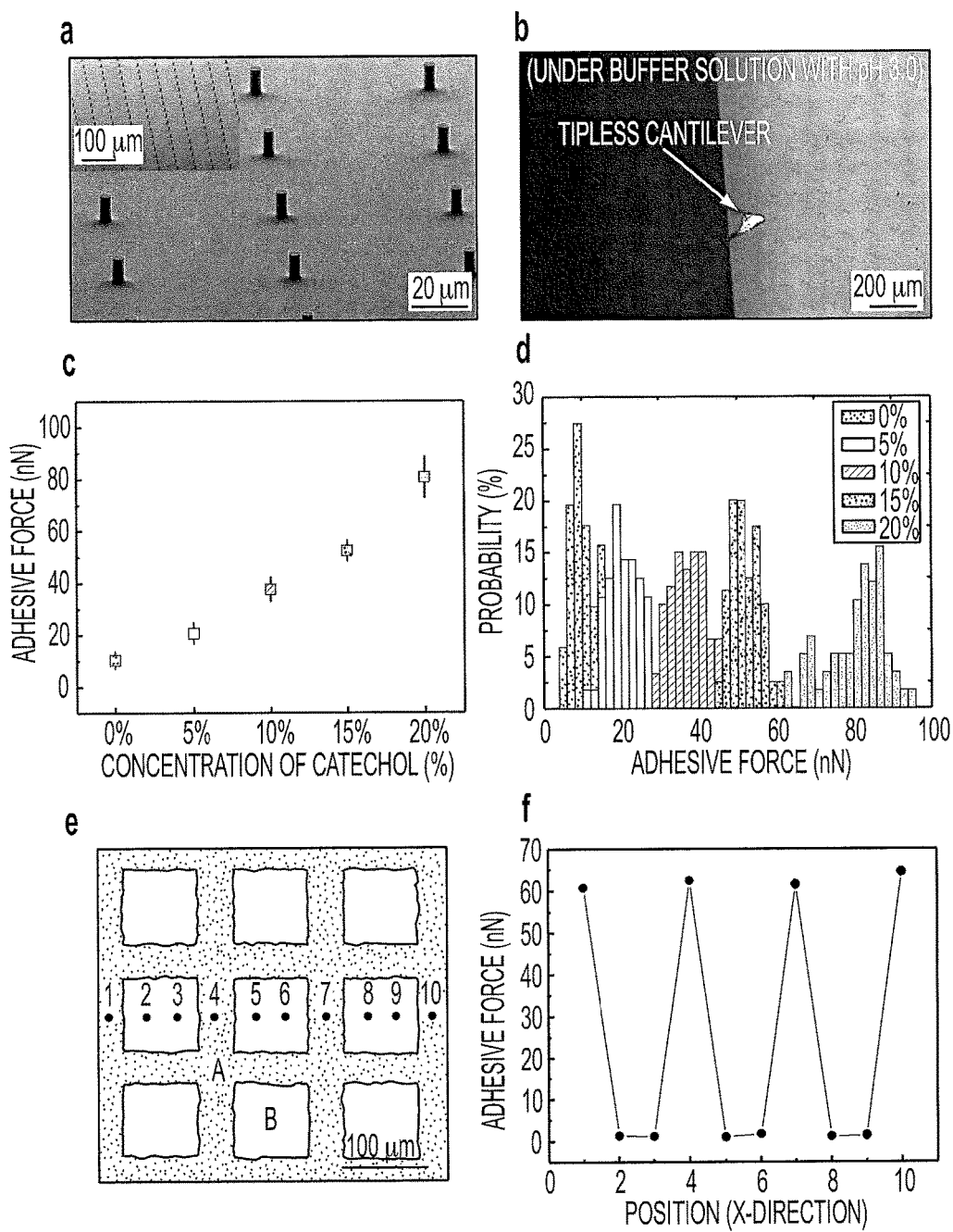
FIG. 9 (a) SEM images of fabricated microstructures with 5 μm diameter and 10 μm height (AR=2), (b) optical microscope image during adhesive force measurement with AFM (tipless cantilever contacts with one post), (c) adhesive strength results and their (d) distributions of fabricated microstructures according to the different concentration of silane deprotected catechol, (e) metal patterned catechol functionalized polysiloxane film (A: catechol functionalized polysiloxane area, B: Ti/Au metal coated area) and (f) measured adhesive force using AFM. (9.81±3.24 nN, 20.23±4.09 nN, 37.82±4.65 nN, 51.94±3.98 nN, and 82.62±7.80 nN).

With prepared SPC-functionalized polysiloxanes bearing both the protected catechol functionality as well as additional thiol functionality, we focused upon transforming them into crosslinked microstructures to prepare pillar array which is adaptive for the design criteria to measure adhesive force of top area of single pillar using atomic force microscopy (AFM). To do so, a liquid pre-polymer mixture of the SPC-functionalized PMMS, triallyl cyanurate (TAC), diacrylate of ethoxylated bisphenol A (BPADMA), and DMPA was poured onto a patterned soft mold and then cured through UV irradiation (λ=365 nm, 4.6 mW cm$^{-2}$) for four minutes under ambient conditions (FIG. 8d). This soft mold was prepared from a hard Si master through soft imprint lithography methods_ENREF_24 using the thiol-ene reaction[34] (FIG. 8a-8c). The photo-cured SPC-functionalized siloxane-based replica films were easily peeled off from the soft mold displaying a lack of adhesion. To ensure that uniform contact area was being measured in each case, we designed pillars with dimensions smaller than the contact area of cantilever (100 μm length and 13.5 μm width) and long enough spacing distance between pillars to provide sufficient separation of each pillars for measuring single pillar adhesion force (FIG. 9b). FIG. 9a shows scanning electron microscopy (SEM) images of fabricated microstructures of SPC-functionalized polysiloxane based materials with 5 μm diameter and 10 μm height (aspect ratio 2).

To show the adhesive ability of the surface of photo-cured SPC-functionalized siloxane films, the surface adhesion force was measured under water using AFM system with a tipless cantilever ($Si_3N_4$) coated with a 10 nm thick layer of titanium oxide since the the bond between titanium oxide surface and catechol single molecule showed one of the strongest non-covalent adhesive force with reversible interaction. E-beam evaporation of Ti onto the tip followed by $O_2$ plasma treatment to form titanium oxide ($TiO_2$) ensured that the surface would experience strong chelation interaction with catecholic moieties on the surface of photo-cured SPC-functionalized siloxane-based films[36]. After titanium oxide coating, the spring constant of each cantilever was calibrated based on their thermal vibration factors before measuring adhesive force. In a typical adhesion experiment, the tipless cantilever was approached to the wet surface of photo-cured siloxane-based films and then the retracting forces versus extensions were measured. The force measurement with AFM were performed under pH 3.0 buffer solution in order to minimize the oxidation of catecholic moieties during the adhesion measurement as well as remove the silyl-protecting group[37] on the surface of the photo-cured siloxane-based films.

Thus, adhesive force indicates the total force between the titania-coated cantilever and the top surface of a single micropillar. After measuring the adhesion with surfaces containing different contact area (i.e. 5, 10, 20 and 50 μm diameter pillars), we found that the 5 μm pillars were best suited to the measurable range of adhesion from our AFM. All adhesive forces were therefore measured using 5 μm diameter pillared surfaces with different incorporations of catechol functionality. Also, to show the rationality between the adhesive force and the concentration of catecholic moieties and demonstrate the synthetic benefits of the controllable concentration of silyl-protected catecholic moieties in photo-cured siloxane-based films, adhesion forces from polysiloxanes with various catechol concentrations were measured with five different ratio (0, 5, 10, 15 and 20 mol % of silyl-protected catecholic moieties) of photo-cured systems by AFM.

The mean values and standard deviations of adhesive forces of single pillar were measured to be 9.81±3.24 nN, 20.23±4.09 nN, 37.82±4.65 nN, 51.94±3.98 nN, and 82.62±7.80 nN, respectively to molar ratio of catecholic moieties (0, 5, 10, 15, and 20 mol %) (FIGS. 9c and 9d). The linear increase of measured adhesive force along with concentration of catechoic moieties indicate that the adhesive forces per single pillar are proportional to the concentration of catecholic moieties and this concentration of the surface of pillars are analogous to the prepared silyl-protected catecholic poly[(mercaptopropyl)methylsiloxane] which means that we can synthesize and functionalize the surface of cured films with a defined number of catecholic moieties as marine organisms do in their various proteins[38].

Finally, as a control, we fabricated masked regions upon the micropatterned adhesive siloxane films and measured the different adhesive forces as a function of masking. In order to evaluate the micropatterned adhesive siloxane films, metal (Ti on Au) film was deposited by E-beam evaporator with transmission electron microscopy (TEM) grid as a shadow mask on the photo-cured siloxane film. FIG. 9e shows a SEM image of photo-cured polysiloxane films patterned with metal film; dark area (A) indicates photo-cured siloxane-based film with catecholic moieties and bright area (B) is metal film evaporated area. FIG. 9f was plotted with the adhesive forces from each area position. Mean value of adhesive force of bright area, metal covered area, was evaluated only to be 5 nN. However, dark area, catecholic moieties included photo-cured siloxane-based film area, has 58 nN adhesive force. These results clearly show the difference of adhesion strength between catechol functionalized areas and metal covered areas and also indicate the versatility and robustness of silane-protected catecholic moieties in polysiloxanes since the adhesive properties of silane-protected catechol moieties are not changed during the micro-patterning process using harsh metal deposition process by E-beam.

Figure 10:
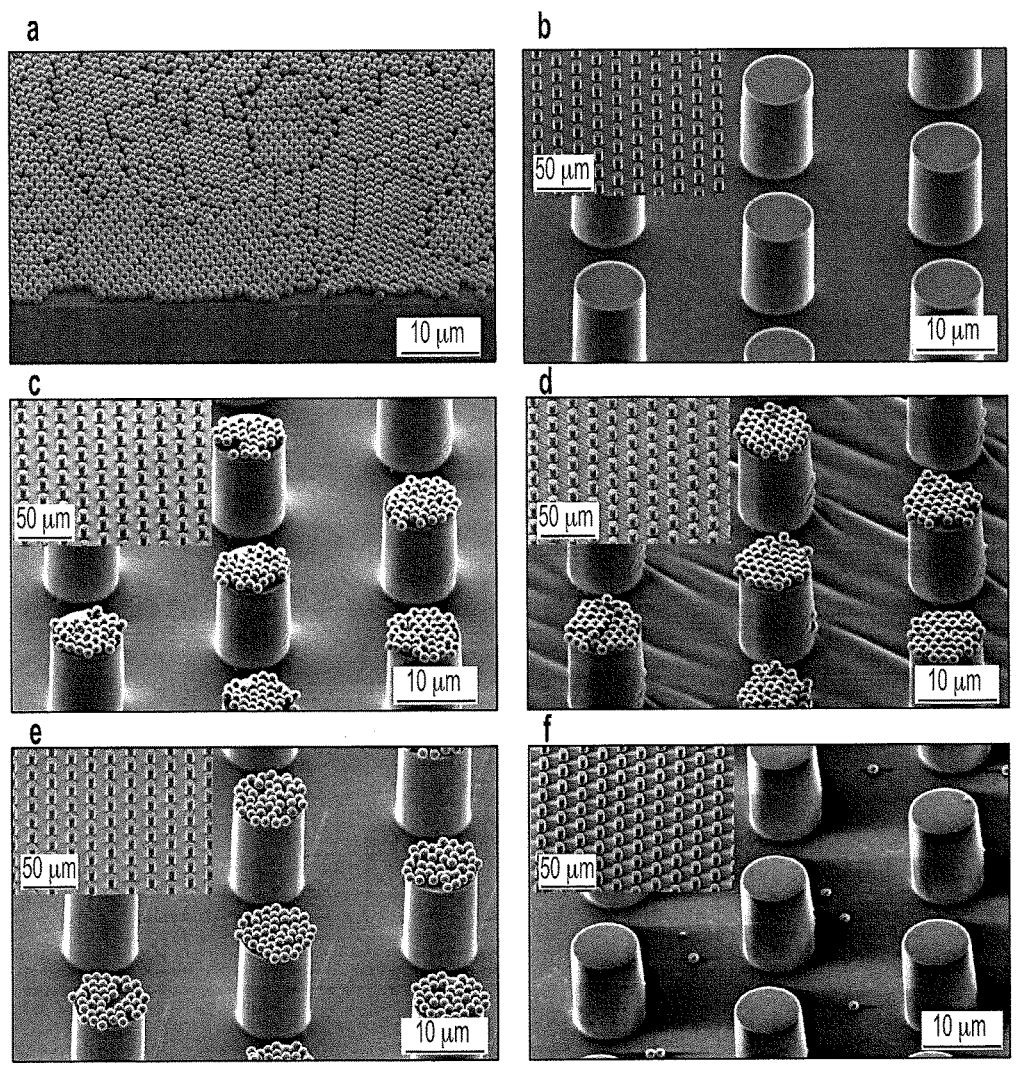
FIG. 10 The representative SEM images of adhesive capability test for using fabricated microstructures and silica beads. (a) silica particles coated the silicon wafer with monolayer, (b) the fabricated microstructures with 10 μm diameter and 30 μm height, directly transferred silica particles on the top of post with silane (c) deprotected and (d) protected polysiloxane, and washed microstructures with silane (e) deprotected and (f) protected polysiloxane using ultrasonicator. Silica particles are well attached with silane deprotected microstructures.

A simple strategy was developed through a combination of the soft imprint lithography[39] and transfer printing[40,41] to prepare 3-dimensional assembled metal oxides structures. The photo-cured adhesive films with pillar arrays were fabricated as described above composed of 10 μm diameter pillars at a height of 30 μm using SPC-functionalized polysiloxanes (FIG. 10b). Following acidic activation of the catechol functionalities on the surface of photo-cured films, the activated films were used to stamp onto a monolayer of silica particles (FIG. 10a) coated on a silicon wafer. In doing so, the silica particles were transferred to the tops of the pillars (FIGS. 10c and 10d); this transfer process was performed using stamps with both silyl protected (non-adhesive) as well as the acid-activated surfaces (adhesive). In the case of the activated surfaces, the silica particles were strongly attached on the top of the posts, remaining anchored even after an extensive washing step. However, in the case of the protected surface, silica particles were completely pulled off from the tops of the posts after the same washing process (FIG. 10f). It appears that the silyl-protected catechols are well protected and cannot provide any adhesiveness, but the adhesiveness of the photo-cured siloxane films are directly activated under acidic condition (pH 3.0 buffer solution) on the top of films and they showed strong adhesiveness to metal oxide surfaces.

Figure 11:
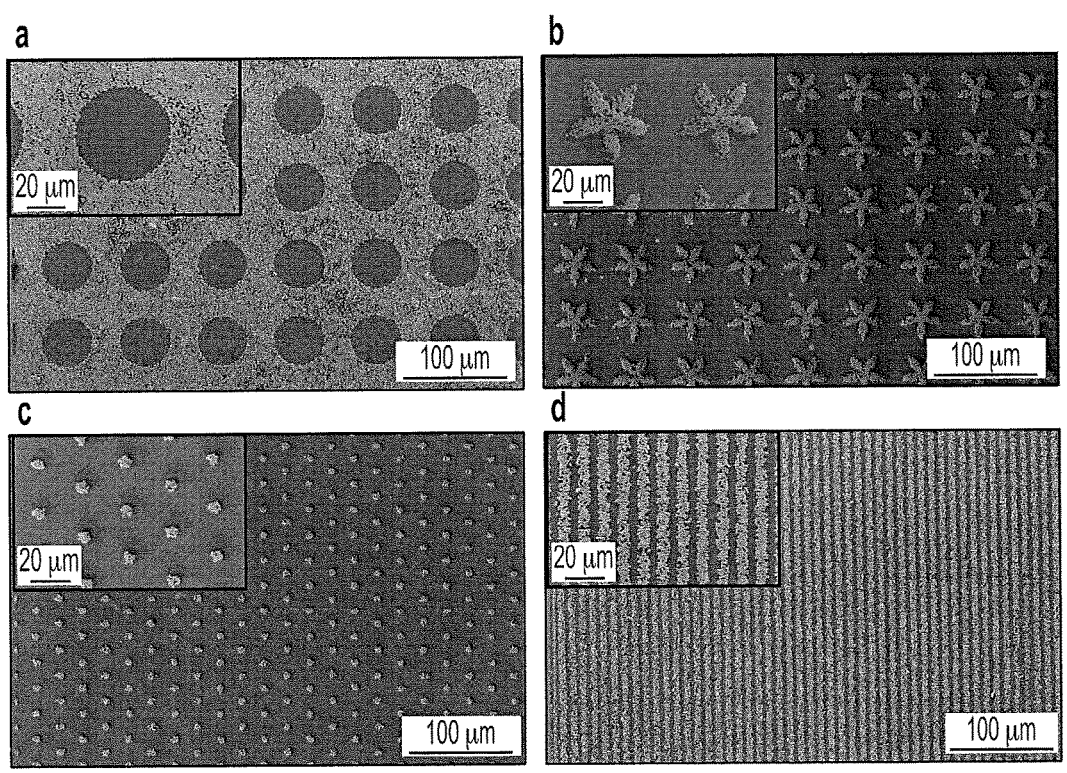
FIG. 11 Representative SEM images of transfer printing using silica beads. (a) 50 um diameter circles, (b) 50 μm flower with square patterns, (c) 7 μm diameter circles with hexagonal patterns and (d) 5 μm line and space patterns.

It is attractive and interesting process to use the prior systems for fabricating surface assembly of metal oxide particles on the surfaces of flexible films inspired by bioadhesive materials. We prepared photo-cured flat films using SPC-functional polysiloxanes. Transfer printing of silica particles was then carried out between a conventional PDMS elastomeric stamp and the adhesive surfaces. In this case, the distinctive difference in surface adhesion forces to metal oxide ensured the effective transfer of silica particles from the stamp to the adhesive surfaces. Using this approach, various patterns of assembled silica nanostructures were patterned facilely onto the adhesive surfaces (FIG. 11) with strong anchoring being resistant to washing and sonication. These results indicate that the surface of photo-cured SPC-functionalized polysiloxane films have enough adhesive strength to retrieve metal oxide particles from the other surfaces such as silicon wafer with silica monolayer or conventional PDMS without considering surface modifier to increase surface energy of target films[42-45].

Figure 12:
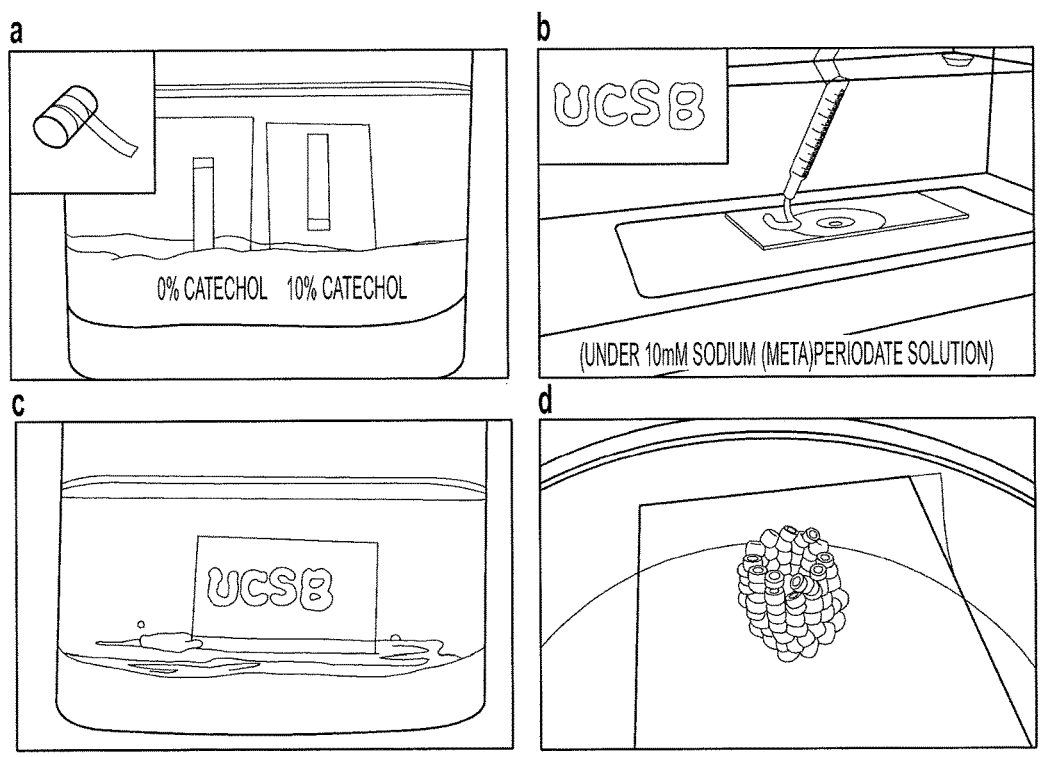
FIG. 12 The other applications of catechol functionalized polysiloxane (a) wet adhesive tape: aluminum bar (50 mm×10 mm×2 mm) was attached on the surface of glass slide under water. Aluminum bar was pressed for overnight under water, (b) injection of liquid-type polysiloxane for formation of structures, (c) formed 2-dimensional and (d) 3-dimensional structures under water using silane deprotected catechol functionalized polysiloxane.
Figure 13:
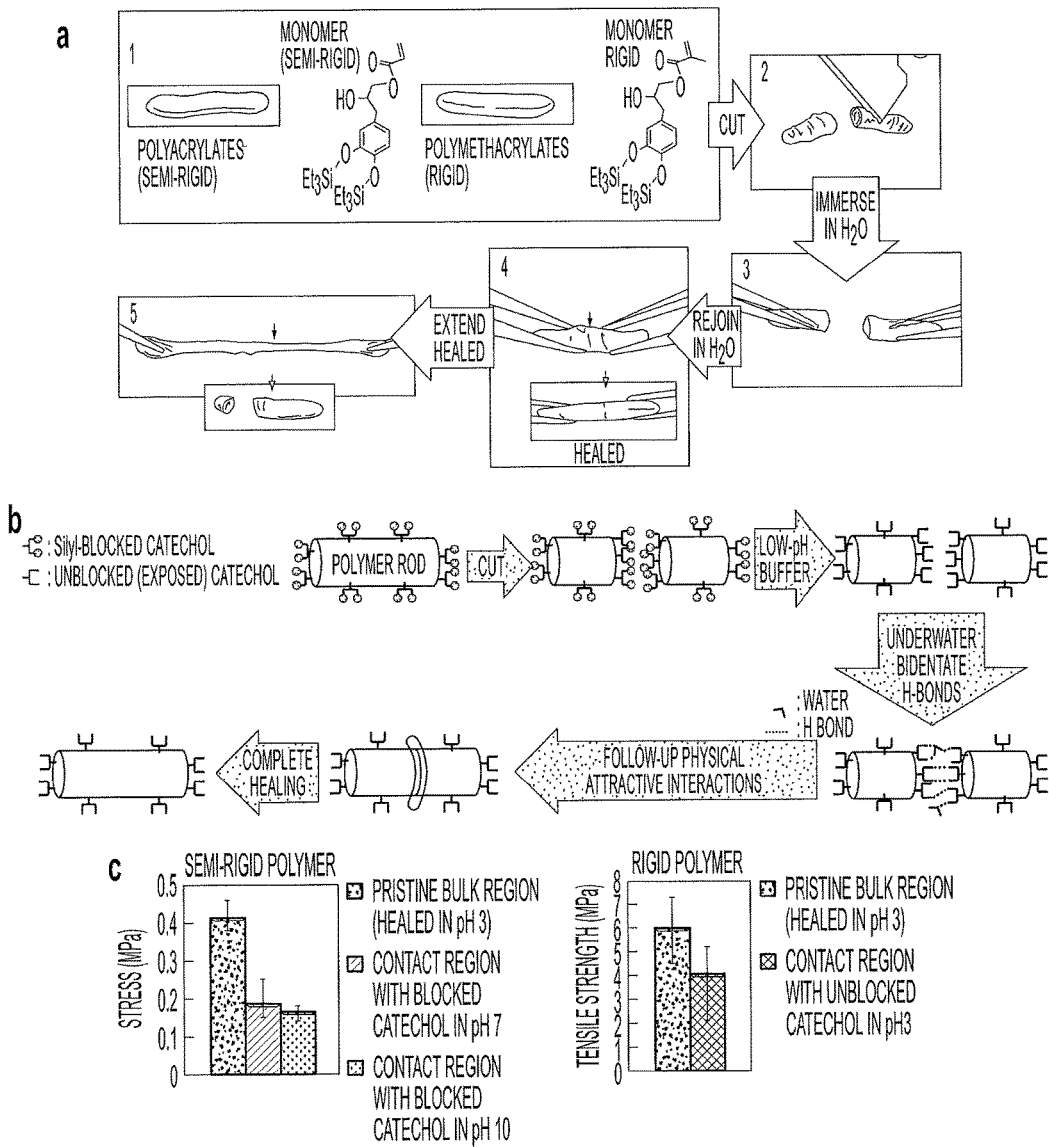
FIG. 13 Schematic diagram of the steps entailed in polymer-rod healing studies. a, Polymer rods (1; semi-rigid, blue rectangle; rigid, red rectangle) were processed as follows: bisected (2), immersed in H$_2$O (pH 3 buffer) at room temperature (3), brought into contact (4) and pulled in tension (5). The blue (semi-rigid) and red (rigid) arrows denote the location of the healed incisions. b, Self-healing scheme. c, Average tensile strength of the samples (error bars indicate standard deviation, n=3).

It should be realized that these SPC-functionalized polysiloxanes are not limited to the preparation of photo-cured films for fabrication of imprint lithography or transfer printing. A significant feature of these catechol functionalized polysiloxanes is the versatility of their application as either moldable solid elastomeric film as well as an uncrosslinked liquid underwater superglue. Indeed, natural marine organisms utilize their adhesive proteins most often as liquid precursors that are injected specifically upon a desired surface. To be able to use the materials for underwater adhesive films, the photo-cured SPC-functionalized polysiloxane-based films were prepared and stored in rolled tape, which were activated under acidic condition before use, and applied between glass slides and aluminum (Al) bar under water and the Al bar was adhered well on the surface of glass slides mediated by prepared under water adhesive tapes (FIG. 12a).

To further emphasize the unique feature of being able to tailor the shape of polysiloxanes as a superglue, liquid polysiloxanes with 50 mol % functionalized with silane-protected catecholic moieties were mixed with commercially available colored sand, followed by deprotection of silane groups with 0.1M HCl aqueous solution. The sand grains were held strongly together within the adhesive polymer, while the mixture remained fluid, easily injected using conventional syringes under 10 mM sodium (meta) periodate solution for accelerated crosslinking between oxidized catechols as well as further reaction with thiol to oxidized catechol[46,47] (FIG. 12b, 12c). When glass beads were used instead of the sand grains, these larger building blocks could be assembled into macroscale objects underwater held in place through the under-water glue catechol polymer (FIG. 12d). These structures are reminiscent of the sand-lined residences of the sandcastle worm enabled through natural DOPA-containing adhesive proteins. These synthetic SPC-functionalized polysiloxane has strong and unique adhesion properties and versatile transformable behaviors and can build various structures with versatile shape of structures.

ADDITIONAL REFERENCES

Each of the following references is hereby incorporated by reference in its entirety.

1 Krivis, A. F. & Chiu, C. C. O. MARINE ADHESIVES—AMINO-ACID CONTENT OF BALANUS-EBURNEUS ADHESIVE. *Microchemical Journal* 34, 284-288, doi:10.1016/0026-265x(86)90122-0 (1986).
2 Waite, J. H. Adhesion a la Moule. *Integrative and Comparative Biology* 42, 1172-1180, doi:10.1093/icb/42.6.1172 (2002).
3 Silverman, H. G. & Roberto, F. F. Understanding marine mussel adhesion. *Mar. Biotechnol.* 9, 661-681, doi:10.1007/s10126-007-9053-x (2007).
4 Waite, J. H. & Tanzer, M. L. POLYPHENOLIC SUBSTANCE OF *MYTILUS-EDULIS*—NOVEL ADHESIVE CONTAINING L-DOPA AND HYDROXYPROLINE. *Science* 212, 1038-1040, doi:10.1126/science.212.4498.1038 (1981).
5 Waite, J. H. & Tanzer, M. L. THE BIOADHESIVE OF *MYTILUS* BYSSUS—A PROTEIN CONTAINING L-DOPA. *Biochem. Biophys. Res. Commun.* 96, 1554-1561, doi:10.1016/0006-291x(80)91351-0 (1980).
6 Polmanteer, K. E. SILICONE-RUBBER, ITS DEVELOPMENT AND TECHNOLOGICAL-PROGRESS. *Rubber Chem. Technol.* 61, 470-502, doi: 10.5254/1.3536197 (1988).
7 Quinn, K. J. & Courtney, J. M. SILICONES AS BIOMATERIALS. *British Polymer Journal* 20, 25-32, doi:10.1002/pi.4980200106 (1988).
8 M. G. Voronokov, V. P. Milenshkevich & Yuzhelevskii, Y. A. *The Siloxane Bond*. (Consultants Bureau, N.Y., 1978).
9 Noll, W. *Chemistry and Technology of Silicones*. (Academic Press, 1968).
10 Abbasi, F., Mirzadeh, H. & Katbab, A. A. Modification of polysiloxane polymers for biomedical applications: a review. *Polym. Int.* 50, 1279-1287, doi:10.1002/pi.783 (2001).
11 Yilgor, I. & J. E. McGrath. *Advances in Organosiloxane Copolymers*. 1-86 (Springer-Verlag, 1988).
12 Lee, H., Lee, B. P. & Messersmith, P. B. A reversible wet/dry adhesive inspired by mussels and geckos. *Nature* 448, 338-U334, doi:10.1038/nature05968 (2007).
13 Blackwell, J. M., Foster, K. L., Beck, V. H. & Piers, W. E. B(C6F5)(3)-catalyzed silation of alcohols: A mild, general method for synthesis of silyl ethers. *J. Org. Chem.* 64, 4887-4892, doi:10.1021/jo9903003 (1999).
14 Chojnowski, J. et al. Mechanism of the B(C6F5)(3)-catalyzed reaction of silyl hydrides with alkoxysilanes. Kinetic and spectroscopic studies. *Organometallics* 24, 6077-6084, doi:10.1021/om050563p (2005).
15 Chojnowski, J., Fortuniak, W., Kurjata, J., Rubinsztajn, S. & Celia, J. A. Oligomerization of hydrosiloxanes in the presence of tris(pentafluorophenyl) borane. *Macromolecules* 39, 3802-3807, doi:10.1021/ma060080c (2006).
16 Thompson, D. B. & Brook, M. A. Rapid assembly of complex 3D siloxane architectures. *Journal of the American Chemical Society* 130, 32-+, doi:10.1021/ja0778491 (2008).
17 Rubin, M., Schwier, T. & Gevorgyan, V. Highly efficient B(C(6)F(5))(3)-catalyzed hydrosilylation of olefins. *J. Org. Chem.* 67, 1936-1940, doi:10.1021/jo016279z (2002).
18 Blackwell, J. M., Sonmor, E. R., Scoccitti, T. & Piers, W. E. B(C6F5)(3)-catalyzed hydrosilation of imines via silyliminium intermediates. *Org. Lett.* 2, 3921-3923, doi:10.1021/ol006695q (2000).
19 Ishihara, K. & Yamamoto, H. Arylboron compounds as acid catalysts in organic synthetic transformations. *Eur. J. Org. Chem.*, 527-538 (1999).
20 Blackwell, J. M., Morrison, D. J. & Piers, W. E. B(C6F5)(3) catalyzed hydrosilation of enones and silyl enol ethers. *Tetrahedron* 58, 8247-8254, doi:10.1016/s0040-4020(02)00974-2 (2002).
21 Gevorgyan, V., Rubin, M., Benson, S., Liu, J. X. & Yamamoto, Y. A novel B(C6F5)(3)-catalyzed reduction of alcohols and cleavage of aryl and alkyl ethers with hydrosilanes. *J. Org. Chem.* 65, 6179-6186, doi:10.1021/jo000726d (2000).
22 Erker, G. Tris(pentafluorophenyl)borane: a special boron Lewis acid for special reactions. *Dalton Trans.*, 1883-1890, doi:10.1039/b503688g (2005).
23 Roesler, R., Har, B. J. N. & Piers, W. E. Synthesis and characterization of (perfluoroaryl)borane-functionalized carbosilane dendrimers and their use as Lewis acid catalysts for the hydrosilation of acetophenone. *Organometallics* 21, 4300-4302, doi:10.1021/om0205187 (2002).
24 Piers, W. E. & Chivers, T. Pentafluorophenylboranes: from obscurity to applications. *Chem. Soc. Rev.* 26, 345-354, doi:10.1039/cs9972600345 (1997).
25 Killops, K. L., Campos, L. M. & Hawker, C. J. Robust, efficient, and orthogonal synthesis of dendrimers via thiol-ene "Click" chemistry. *Journal of the American Chemical Society* 130, 5062-+, doi:10.1021/ja8006325 (2008).
26 Campos, L. M. et al. Development of thermal and photochemical strategies for thiol-ene click polymer functionalization. *Macromolecules* 41, 7063-7070, doi:10.1021/ma801630n (2008).

27 Gress, A., Volkel, A. & Schlaad, H. Thio-click modification of poly 2-(3-butenyl)-2-oxazoline. *Macromolecules* 40, 7928-7933, doi:10.1021/ma071357r (2007).

28 Justynska, J. & Schlaad, H. Modular synthesis of functional block copolymers. *Macromol. Rapid Commun.* 25, 1478-1481, doi:10.1002/marc.200400228 (2004).

29 David, R. L. A. & Kornfield, J. A. Facile, efficient routes to diverse protected thiols and to their deprotection and addition to create functional polymers by thiol-ene coupling. *Macromolecules* 41, 1151-1161, doi:10.1021/ma0718393 (2008).

30 ten Brummelhuis, N., Diehl, C. & Schlaad, H. Thiol-Ene Modification of 1,2-Polybutadiene Using UV Light or Sunlight. *Macromolecules* 41, 9946-9947, doi:10.1021/ma802047w (2008).

31 Hoyle, C. E., Lee, T. Y. & Roper, T. Thiol-enes: Chemistry of the past with promise for the future. *J Polym. Sci. Pol. Chem.* 42, 5301-5338, doi:10.1002/pola.20366 (2004).

32 Kang, T. et al. Facile access to internally functionalized dendrimers through efficient and orthogonal click reactions. *Chem. Commun.* 46, 1556-1558, doi:10.1039/b921598k (2010).

33 Amir, R. J. et al. Multifunctional Trackable Dendritic Scaffolds and Delivery Agents, *Angew. Chem.-Int. Edit.* 50, 3425-3429, doi:10.1002/anie.201007427 (2011).

34 Campos, L. M. et al. Highly Versatile and Robust Materials for Soft Imprint Lithography Based on Thiol-ene Click Chemistry. *Advanced Materials* 20, 3728-+, doi:10.1002/adma.200800330 (2008).

35 Markowitz, K., Moynihan, M., Liu, M. S. & Kim, S. BIOLOGIC PROPERTIES OF EUGENOL AND ZINC OXIDE-EUGENOL—A CLINICALLY ORIENTED REVIEW. *Oral Surgery Oral Medicine Oral Pathology Oral Radiology and Endodontics* 73, 729-737, doi:10.1016/0030-4220(92)90020-q (1992).

36 Lee, H., Scherer, N. F. & Messersmith, P. B. Single-molecule mechanics of mussel adhesion. *Proceedings of the National Academy of Sciences of the United States of America* 103, 12999-13003, doi:10.1073/pnas.0605552103 (2006).

37 PETER G. M. WUTS, T. W. G. *Greene's Protective Groups in Organic Synthesis*. 4 edn, (John Wiley & Sons, 2006).

38 Waite, J. H., Andersen, N. H., Jewhurst, S. & Sun, C. J. Mussel adhesion: Finding the tricks worth mimicking. *J. Adhes.* 81, 297-317, doi:10.1080/00218460590944602 (2005).

39 Odom, T. W., Love, J. C., Wolfe, D. B., Paul, K. E. & Whitesides, G. M. Improved pattern transfer in soft lithography using composite stamps. *Langmuir* 18, 5314-5320, doi:10.1021/la0201691 (2002).

40 Kim, T.-H. et al. Full-colour quantum dot displays fabricated by transfer printing. *Nature Photonics* 5, 176-182, doi:10.1038/nphoton.2011.12 (2011).

41 Meitl, M. A. et al. Transfer printing by kinetic control of adhesion to an elastomeric stamp. *Nature Materials* 5, 33-38, doi:10.1038/nmat1532 (2006).

42 Gates, B. D. et al. New approaches to nanofabrication: Molding, printing, and other techniques. *Chem. Rev.* 105, 1171-1196, doi:10.1021/cr030076o (2005).

43 Geissler, M. & Xia, Y. N. Patterning: Principles and some new developments. *Advanced Materials* 16, 1249-1269, doi:10.1002/adma.200400835 (2004).

44 Xia, Y. N. & Whitesides, G. M. Soft lithography. *Annu. Rev. Mater. Sci.* 28, 153-184, doi:10.1146/annurev.matsci.28.1.153 (1998).

45 Xia, Y. N. & Whitesides, G. M. Soft lithography. *Angew. Chem.-Int. Edit.* 37, 551-575 (1998).

46 Lee, H., Dellatore, S. M., Miller, W. M. & Messersmith, P. B. Mussel-inspired surface chemistry for multifunctional coatings. *Science* 318, 426-430, doi:10.1126/science.1147241 (2007).

47 Yu, J. et al. Mussel protein adhesion depends on inter-protein thiol-mediated redox modulation. *Nat. Chem. Biol.* 7, 588-590, doi:10.1038/nchembio.630 (2011).

FURTHER EXAMPLES

To better assess the contribution of catechol to polymer self-healing in a reducing (pH 3), metal-free wet environment, we prepared a material from common, water-insoluble synthetic acrylic polymers having a catechol-functionalized surface. These materials are completely self-healing in a process initiated by catechol-mediated interfacial hydrogen bonding, and consolidated by follow up interactions (for example, hydrophobic and steric) after a brief compression ($\sim 6 \times 10^4$ Pa). The crucial and robust roles played by catecholic hydrogen bonding in re-establishing contact between the fragments, then giving way to other interactions, were completely unexpected and may inspire the wet repair of other polymers and tissues.

Some self-healing polymers are described in, for example, "Surface-initiated self-healing of polymers in aqueous media," Ahn, B K., et al., *Nature Materials*, Advance Online Publication, Jul. 27, 2014, DOI: 10.1038/NMAT4037, which is incorporated by reference in its entirety.

Surface rearrangement plays a critical role in polymeric interface properties[17]; therefore, two polymers with different moduli were prepared to study the surface changes initiated during self-healing. Semi-rigid (Young's modulus, E~1.3 MPa) and rigid polymer rods (E~350 MPa) were cast from triethylsilane-blocked catecholacrylate and catecholmethacrylate monomers, respectively, by free radical ultraviolet polymerization.

Figure 14:
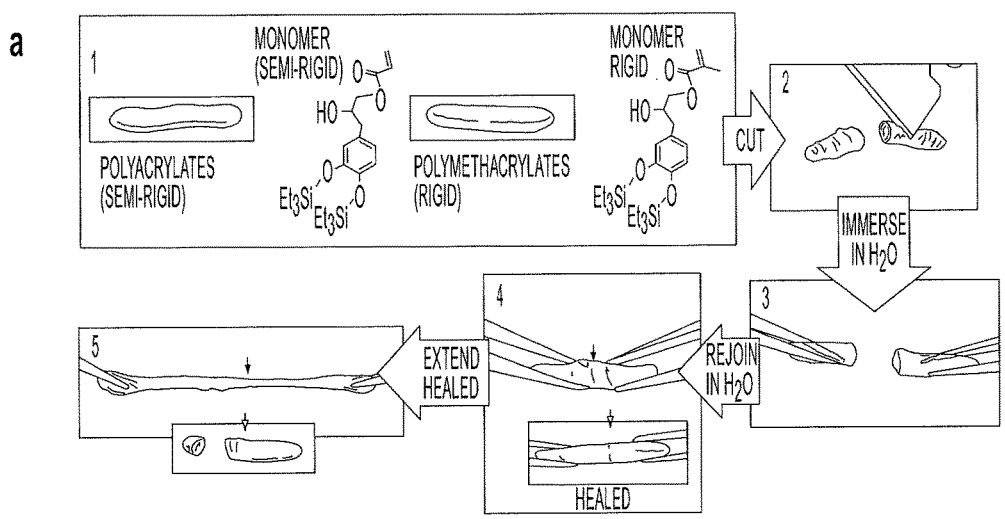
FIG. 14 NEXAFS spectra of catechol-functionalized polymer samples at incident radiation angles ranging from 30° to 120°. a,b, Partial electron yields for exposed (a) and blocked (b) catecholic polymer. The dashed circles indicate the peaks whose intensities are plotted in c. c, π* orbitals plot. Error bars indicate the maximum uncertainty (~2%) of the electron yield. d, Incident radiation angle at 120°.

The rods were bisected using a new scalpel blade; the two pieces were soaked in a series of dilute buffers with increasing pH (range: 3-10), respectively, for 20 min. Subsequently, the cut ends were rejoined under light compression ($\sim 6 \times 10^4$ Pa) for 2 min in water (pH 3, 7 or 10). pH 3 activates the catechol functionalities on the surfaces by removing the triethylsilyl-protecting groups[14] (FIG. 14), whereas triethylsilyl catechols at pH 7 and 10 remain blocked (protected). Catechols internalized in the bulk remained blocked at all conditions (pH 3, 7 and 10). To avoid catechol oxidation and related ring coupling, experiments involving exposed surface catechols were performed at pH 3, where the high quinone reduction potential ($E_0 \sim 0.38$V; ref. 18) assures catechol stability[19].

Semi-rigid rods with exposed surface catechols never failed near the contact region, whereas rigid rods sometimes ruptured in the contact region (FIG. 14a,b). In the latter case, when breakage occurred in the contact region, the two pieces were repeatedly brought into contact and pulled in tension until a non-contact breakage occurred. During cyclic testing, the healed (the contact region) and undamaged portions of the rigid polymer rods exhibited similar mechanical properties (FIG. 14c). When surface treatments and experiments were carried out at pH 7 and 10, catechols remained blocked by silyl protection. Under these conditions, the semi-rigid polymer rods with blocked surface catechols always failed in the contact area, whereas the rigid polymer rods with blocked surface catechols showed no bonding whatever (FIG. 14c). These results highlighted the importance of catechols at the self-healing interface, and suggested that only reversible interactions (for example, hydrogen bonds) took place during the initial stages of self-healing.

The Bell theory predicts that a bidentate hydrogen bond, such as that between a catechol donor and a surface acceptor, has a binding lifetime that is $10^6$ times longer than the monodentate hydrogen-bond[20]; experiment confirms that the catechol-mediated bidentate hydrogen bond is stronger than the monodentate hydrogen bond (that is, $E_{bidentate}\sim2E_{monodentate}$, or $\tau_{bidentate}\sim10^6\tau_{monodentate}$) (refs 13,20). In addition, previous studies of the intermolecular hydrogen bonds between phenolic hydroxyls[21], catechol and quinone22 in storage devices (ferroelectrics), two neighboring catechols (hydrogen-bond length 2.12 Å, ~3.0 kJmol$^{-1}$; ref. 23), and multivalent intermolecular hydrogen bonds of catechols in water[24], concur that closely stacked catechols at surfaces provide strong intermolecular hydrogen bonds when brought into contact.

Figure 15:
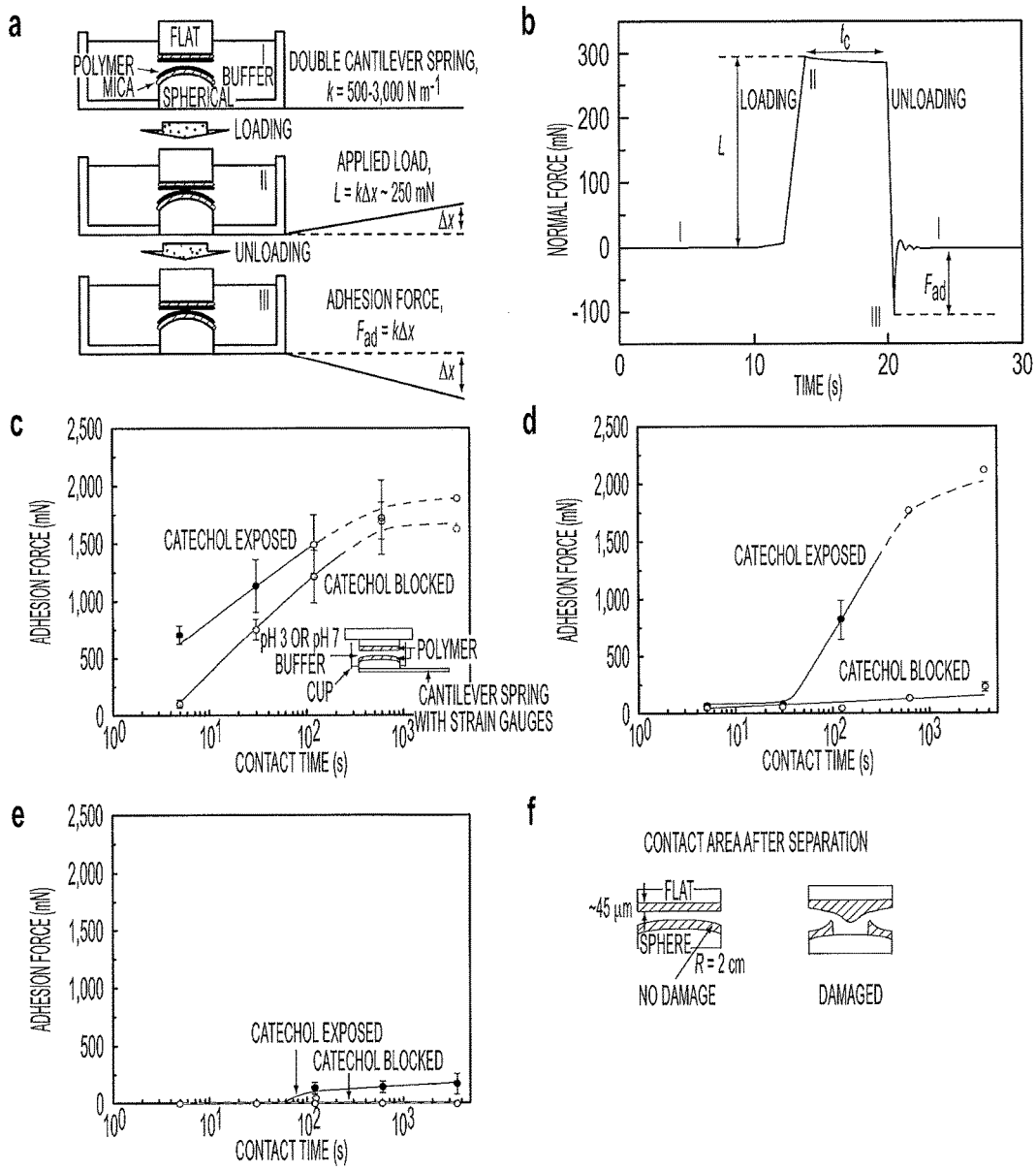
FIG. 15 Cohesive interactions between polymer films functionalized with exposed and blocked catechols as measured by the surface forces apparatus. a, Schematic of the symmetric surface geometry. b, An example of the measured normal-force signal when the surfaces are not in contact (I), and during loading (II) and unloading (III). c-e, Plots showing the force adhesion $F_{ad}$ versus contact time $t_c$ under an applied preload of L~250 mN, between two soft/mobile (c), semi-rigid (d), and rigid polymeric surfaces (e). In c,d, the dashed lines and open circles indicate that polymer in the contact region becomes damaged on separation as shown in f. f, Schematics of undamaged and damaged surfaces.

The synchrotron near-edge X-ray absorption fine structure (NEXAFS; FIG. 15) of the polymers confirms that catechol moieties existed only at the polymer/water interface, whereas catechols buried in the bulk remained silyl-blocked. It is noteworthy that of the analytical methods used, including synchrotron grazing incidence wide-angle X-ray scattering, X-ray reflectivity, and confocal Raman microscopy, only synchrotron NEXAFS (highly surface sensitive) detected small surface-associated intensity changes (FIG. 15). The others were unable to differentiate the interface from the bulk. In NEXAFS, a plot of the π* intensity in polymers with exposed catechols increased slightly with an increasing incident angle (FIG. 15b), indicating a slightly ordered orientation of aromatic rings on the surface, whereas in polymers with blocked catechols random distribution is evident[25,26] (FIG. 15c). In addition, the π* orbital signal was more pronounced for polymers with exposed catechols compared with the blocked controls (FIG. 15d), suggesting that removal of the silyl groups may enable more catechols to populate the interface. Given the low uncertainty of the NEXAFS measurements, the differences are likely to be significant[25,26]. Consistent with NEXAFS, X-ray photoelectron spectroscopy showed ~10% decrease in the Si 2p signal following acid treatment.

Contact-angle measurements of water droplets on all prepared polymer surfaces indicate a decreasing hydrophobicity with time, suggesting that the polymeric surfaces are undergoing a reversible rearrangement[17]. These surface group 'turnover' effects are known to change the interfacial adhesion energy and, therefore, the contact angle. Increasing adhesion with contact time, $t_c$, has been seen in many systems[27]. These phenomena directly depend on bulk and (especially surface) molecular mobility, stiffness, and viscosity of the material, and determine the time frame in which an increase in adhesion starts and plateaus.

To elucidate the interfacial mechanism of adhesion related to self-healing, a surface forces apparatus (SFA) was used to investigate the contact time ($t_c$)-dependent adhesion at the interface of the self-healing (contact) area (FIG. 16a,b).

Figure 16:
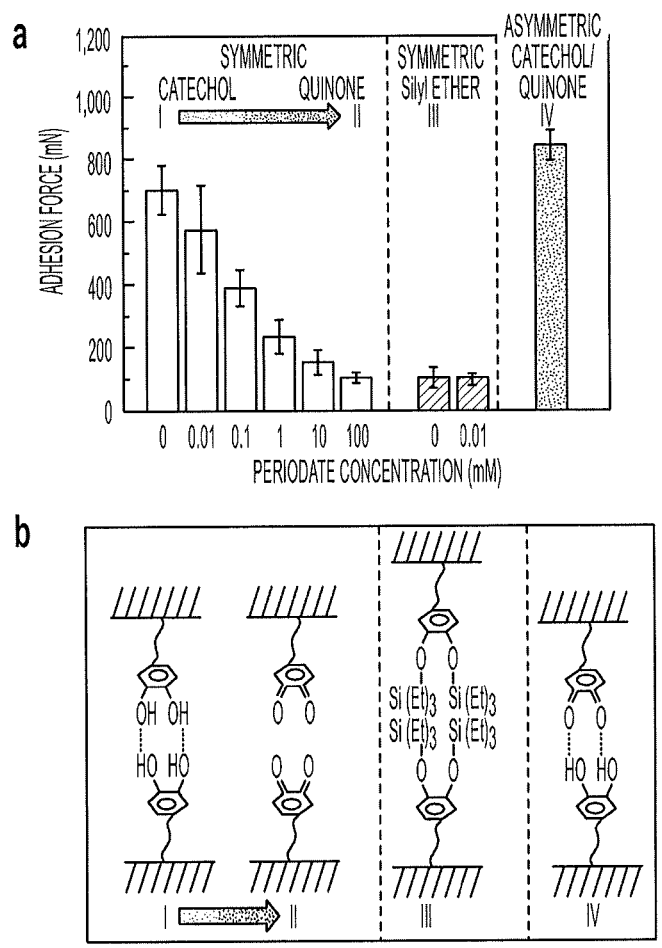
FIG. 16 Adhesion force between various polymeric surfaces with a contact time of 5 s and 250 mN of applied load. a, Catechol surfaces are partially (I) or fully (II) oxidized to quinone surfaces by adding different concentrations (0.01-100 mM) of periodate. Error bars indicate standard deviation, n=5. b, Proposed interfacial chemistry for I, II, III and IV.

Adhesion forces ($F_{ad}$) between symmetric surfaces were measured as a function of $t_c$ (FIG. 16) at a fixed load (L) of 250 mN. For soft polymers (synthesized as the semi-rigid polymer but with lower polymerization), $F_{ad}$ of the exposed and blocked catecholic polymers increased monotonically with time from 700 to 1,500 mN and from 100 to 1,210 mN, respectively, with $t_c$ increasing from 5 to 120 s (FIG. 16c). After a contact time of $t_c\sim120$ s, the $F_{ad}$ between two exposed catecholic polymer surfaces (film thickness~25 μm) exceeded the $F_{ad}$ of the same polymer to a glass disc ($F_{ad}\sim1,500$ mN for these asymmetric surfaces), and resulted in polymer damage during detachment (FIG. 16f). In contrast, a $t_c\sim600$ s was required for the blocked catecholic polymer to exhibit the same level of damage on detachment.

In the case of the semi-rigid polymers (FIG. 16d), owing to the increase in polymer stiffness, $F_{ad}$ of both the exposed and blocked catecholic polymers exhibited a low $F_{ad}$ of ~50-70 mN up to a 'critical' $t_c$ of 30 and 120 s, respectively. After the critical $t_c$, $F_{ad}$ of the exposed catecholic polymer monotonically increased up to 820 mN at $t_c=120$ s, whereas with blocked catechols $F_{ad}$ increased to only 230 mN at $t_c=3,600$ s. Also, the contact surface of the blocked catecholic polymer remained undamaged during detachment up to a $t_c=3,600$ s (FIG. 16f).

For the rigid polymers (FIG. 16e), the effects of the low molecular mobility were more pronounced. No increase in $F_{ad}$ was observed for the blocked catecholic polymer up to $t_c=3,600$ s, whereas exposed catecholic polymers had a critical $t_c\sim50$ s, which was larger than in the semi-rigid polymer. Consequently, $F_{ad}$ increased to only 180 mN at $t_c=3,600$ s in the rigid polymers.

Previous studies have proposed that the self-healing adhesion of catechol-functionalized polymers and proteins relies on the bidentate hydrogen bonding of catechols as well as on hydrophobic contributions[13,20,28]. If the same is true for catecholic polyacrylates, then molecular and polymer mobility should be important contributing factors. From the time-dependent adhesion tests (FIG. 16), we can conclude the following. First, bulk and surface molecular rearrangements are required to enable hydrogen bonding. The existence of a critical $t_c$ indicates that the rearrangement/reorientation of polymer chains and molecular groups is a requisite for extensive interfacial hydrogen bonding. That the critical $t_c$ increases with decreasing bulk and molecular mobility further supports this conclusion. Second, hydrogen bond formation accelerates other attractive interactions. For the blocked catecholic semi-rigid polymer, $F_{ad}$ increased only slightly (=230 mN m$^{-1}$ at $t_c=3,600$ s), whereas the adhesion of exposed catecholic polymer (FIG. 16d) increased from 70 to 820 mN at $t_c=120$ s, which is significantly greater than the hydrogen-bond contribution of $F_{ad}\sim300$ mN ($F_{ad,exposed}-F_{ad,blocked}$) measured for soft polymers at $t_c=120$ s. This suggests that below a certain bulk/molecular mobility, hydrogen bonding is required to mobilize the other attractive interactions (for example, van der Waals, hydrophobic, polymer interdigitation, interpenetration, and interdiffusion) for self-healing.

Periodate stoichiometrically oxidizes catechol to quinone[29], hence was used to perturb intermolecular hydrogen bonding between symmetric catecholic soft polymer films (FIG. 17). With a $t_c=5$ s and L=250 mN, the soft polymer films achieved a $F_{ad}=700$ mN. This force decreased monotonically with increasing concentration of periodate (FIG. 17I,II), ranging from all catechols (at 0 mM periodate; FIG. 17I) to all quinones (at 100 mM periodate; FIG. 17II). The latter resembled that of blocked catecholic polymers (FIG. 17a-III,b-III), suggesting no catecholic hydrogen-bond contribution to adhesion. The importance of hydrogen bonding is further underscored by the adhesion tests using asymmetric film chemistry in which an all-catechol surface was brought into contact with an all-quinone surface (FIG. 17a-IV,b-IV). As this allows every catechol donor to hydrogen-bond to a quinone acceptor, this configuration gave forces comparable to or higher than those of symmetric catechol-catechol surfaces, where the catechols are both acceptors and donors.

The adhesion force from pure hydrogen bonding ($F_{ad,catechol/catechol}-F_{ad,quinone/quinone}$) was calculated to be 600 mN at $t_c=5$ s. The catecholic bidentate hydrogen bond[30] has previously been reported to be around 67±11 pN, which gives a catechol surface density of $\Gamma=4.6\times10^{16}$ m$^{-2}$ and a contact diameter of 0.5 mm in a contact about to detach. Assuming a flat surface with catechols distributed in a square lattice, the spacing between exposed catechols would be $\delta=(1/\Gamma)^{1/2}\approx4.7\pm0.4$ nm. The high density of catechols at the interface is further compelling evidence for hydrogen-bond-initiated self-healing. However, we must emphasize that this prediction is valid only when intermolecular bidentate hydrogen bonding occurs, and some degree of multivalent hydrogen bonding is highly likely[24] (FIG. 14b).

Complete underwater self-healing in catechol-functionalized polyacrylates is initiated by intermolecular hydrogen bonding between interfacial catechol moieties, and subsequently consolidated by the recruitment of deeper physical interactions. This mechanism may explain the unusually strong and reversible adhesion measured between two dopa-containing mfp-5 films under reducing conditions[29]. More critically, it shows how simply re-engineering the surface of polyacrylate-based biomaterials can result in superior bulk self-mending properties. The need for improved self-mending in polyacrylates, for example, PMMA, is widely recognized[5]. Although the self-mending described here is limited to compliant materials at present, it holds considerable promise for the design of more durable implants in the future[6].

Methods

To prepare the underwater self-healing polymers, silane-protected eugenol acrylates and silane-protected methacrylates were synthesized by silane protection of eugenol[14], epoxidation[31,32] and acrylation[33] of the alkene group, followed by ultraviolet radical polymerization.

Ultraviolet radical polymerization was carried out with the Fusion ultraviolet system (Gaithersburg) that consisted of a 300 W inch$^{-1}$ (2.54 cm) H lamp and LC6B benchtop conveyor belt. We prepared the polymers with a photoinitiator (Irgacure 819, bis-(2,4,6-trimethylbenzoyl)-phenyl-phosphineoxide), which was generously provided by BASF (Florham Park). Irgacure 819 at 1 wt % (0.01 g) was added to neat 1 or 2 (1 g) and the mixture was coated (thickness 25 μm) onto a substrate. Soft polymer sample was produced from 1 with 4 ultraviolet scans (ultraviolet radiation dose: 2,460-2,640 mJ cm$^{-2}$) whereas semi-rigid polymer required 8 scans (ultraviolet radiation dose: 4,920-5,280 mJ cm$^{-2}$). Rigid polymer sample was produced from 2 with 8 scans (ultraviolet radiation dose: 4,920-5,280 mJ cm$^{-2}$).

The tensile strength (stress at break) was measured with a Bionix 200 tensile tester (MTS Systems). The polymer rods with 5 mm diameters were prepared by casting and kneading from the ultraviolet polymerized polymer films on a Teflon liner. The tensile strength distinguished the semi-rigid polymer with acrylate backbone and the rigid polymer with methacrylate backbone We bisected each polymer rod with a clean razor blade, and then soaked the pieces in buffers of different pH (pH 3, 7 and 10); the silyl-protecting groups of the catechols at the polymer surface were conveniently removed at low pH (pH 3 buffer) as previously reported[14] to expose superficial catechol moieties. It is unlikely that the pH 3 buffer removes all silyl groups at the interface; thus, quantification and optimization of silyl deprotection will require further future work. Subsequently, the tensile strength of each sample was measured to study the self-healing effect of surface catechol functionalities using an MTS tensile tester.

NEXAFS were performed at the NIST/Dow soft X-ray materials characterization facility, beamline U7A at the National Synchrotron Light Source (NSLS) of Brookhaven National Laboratory. Carbon K-edge partial electron yield data were collected at a grid bias of −150V.

Contact angle measurements were performed using a custom-built contact angle goniometer. A sealed contact angle chamber was built of glass, and Teflon. A syringe needle was inserted through a hole at the top Teflon cap of the chamber and delivery was controlled from the outside by a motorized syringe device (KDS LEGATO270, Kd Scientific). A video camera was used to record the image of the drop. The air inside the chamber was saturated with water vapour for 30 min before experiments, maintaining the humidity at ~85%. The water droplet was infused for 2 min with the constant volumetric flow rate of 5 μl min$^{-1}$ and was in rest for 60 min. The contact angle decreased with time (from 138° to 119°) and a three-phase contact line consequently crept out. Contact line creep is an indicator of molecular turnover of polymers at the surface, for example, emersion of less hydrophobic polymers. The initial hydrophobicity returned when the surface was dried, suggesting a reversible rearrangement of the polymeric surfaces.

In the SFA experiments, two glass discs (one spherical with R=2 cm, and one flat) were thoroughly cleaned with chloroform and ethanol. The spherical disc was firstly mounted into a custom-made 'cup' (FIG. 16a) before polymer deposition. The monomers (silane-protected eugenol acrylates or silane-protected methacrylates) were spread onto the glass discs and ultraviolet cured for predetermined times to achieve soft, semi-rigid or rigid polymeric surfaces (see ultraviolet polymerization section for details). For the contact time dependence experiment (FIG. 16), no additional modification was performed before mounting the surfaces into the SFA.

For the experiment to check the effect of catechol oxidation (FIG. 17), catechol moieties at the surface were unblocked by soaking in pH 3 buffer for 30 min. Oxidation of catechols to orthoquinones was obtained by exposure to 0.01 mM-100 mM of periodate solution in pH 3 buffer for 10 min. The surfaces prepared as above were mounted in an SFA 2000 (ref. 34) attached with semiconductive strain gauges at double cantilever springs for load measurement[35]. Both surfaces were kept immersed in treatment buffer (pH 3 sodium acetate or pH 7 phosphate) using a miniaturized 'cup', which contains buffer reservoir (FIG. 16a). Loading and unloading were performed using a coarse micrometer which gives a maximum displacement of 0.5 cm at the velocity of ~2 mm s$^{-1}$. Depending on the stiffness of the double cantilever spring (up to ~3,000N m$^{-1}$), this system can measure adhesion forces up to ~15 N. Applied load is determined by a change of the normal force signal to the positive direction and adhesion (pull out) force was measured by the negative normal force signal at which it jumped to zero normal force (FIG. 16b).

For the first set of experiments (FIG. 16), after loading, the system was equilibrated for an adjustable contact time $t_c$ (5-3,600 s) before unloading, to investigate the relation between the polymer rigidity, contact time and adhesion force. After unloading, the lower surface was dismounted from the SFA to check for damage. For the second set of experiments (FIG. 17), a fixed $t_c=5$ s was applied, and different surfaces were investigated to study the effects of hydrogen bonding on adhesion force. Applied loads L were set to 250 mN for all cases.

FURTHER REFERENCES

Each of the following references is hereby incorporated by reference in its entirety.

1. White, S. R, et al. Autonomic healing of polymer composites. Nature 409, 794-797 (2001).
2. Ghosh, B. & Urban, M. W. Self-repairing oxetane-substituted chitosan polyurethane networks. Science 323, 1458-1460 (2009).
3. Chen, X. X. et al. A thermally re-mendable cross-linked polymeric material. Science 295, 1698-1702 (2002).
4. Cordier, P., Tournilhac, F., Soulie-Ziakovic, C. & Leibler, L. Self-healing and thermoreversible rubber from supramolecular assembly. Nature 451, 977-980 (2008).
5. Dailey, M. M. et al. A self-healing biomaterial based on free-radical polymerization. J. Biomed. Mater. Res. http://dx.doi.org/10.1002/jbm.a.34975 (2013).
6. Boger, A., Heini, P., Windolf, M. & Schneider, E. Adjacent vertebral failure after vertebroplasty: A biomechanical study of low-modulus PMMA cement. Eur. Spine J. 16, 2118-2125 (2007).
7. Holten-Andersen, N. et al. pH-induced metal-ligand cross-links inspired by mussel yield self-healing polymer networks with near-covalent elastic moduli. Proc. Natl Acad. Sci. USA 108, 2651-2655 (2011).
8. Krogsgaard, M., Behrens, M. A., Pedersen, J. S. & Birkedal, H. Self-healing mussel-inspired multi-pH-responsive hydrogels. Biomacromolecules 14, 297-301 (2013).
9. Shafiq, Z. et al. Bioinspired underwater bonding and debonding on demand. Angew. Chem. Int. Ed, 51, 4332-4335 (2012).
10. Zeng, H., Hwang, D. S., Israelachvili, J. N. & Waite, J. H. Strong reversible $Fe^{3+}$-mediated bridging between dopa-containing protein films in water. Proc. Natl Acad. Sci. USA 107, 12850-12853 (2010).
11. Holten-Andersen, N., Fantner, G. E., Hohlbauch, S., Waite, J. H. & Zok, F. W. Protective coatings on extensible biofibres. Nature Mater. 6, 669-672 (2007).
12. Carrington, E. & Gosline, J. M. Mechanical design of mussel byssus: Load cycle and strain rate dependence. Am. Malacol. Bull. 18, 135-142 (2004).
13. Yu, J. et al. Mussel protein adhesion depends on interprotein thiol-mediated redox modulation. Nature Chem. Biol. 7, 588-590 (2011).
14. Heo, J. et al. Improved performance of protected catecholic polysiloxanes for bioinspired wet adhesion to surface oxides, J. Am. Chem. Soc. 134, 20139-20145 (2012).
15. Menyo, M. S., Hawker, C. J. & Waite, J. H. Versatile tuning of supramolecular hydrogels through metal complexation of oxidation-resistant catechol-inspired ligands. Soft Matter. 9, 10314-10323 (2013).
16. Sedó, J., Saiz-Poseu, J., Busqué, F. & Ruiz-Molina, D. Catechol-based biomimetic functional materials. Adv. Mater. 25, 653-701 (2013).
17. Belman, N., Jin, K. J., Golan, Y., Israelachvili, J. N. & Pesika, N. S. Origin of the contact angle hysteresis of water on chemisorbed and physisorbed self-assembled monolayers. Langmuir 28, 14609-14617 (2012).
18. Eslami, M., Zare, H. R. & Namazian, M. Thermodynamic parameters of electrochemical oxidation of L-DOPA: Experimental and theoretical studies. J. Phys. Chem. B 116, 12552-12557 (2012).
19. Lee, B. P., Messersmith, P. B., Israelachvili, J. N. & Waite, J. H. in Annual Review of Materials Research Vol. 41 (eds Clarke, D. R. & Fratzl, P.) 99-132 (Annual Reviews: Palo Alto. 2011).
20. Yu, J. et al. Adaptive hydrophobic and hydrophilic interactions of mussel foot proteins with organic thin films. Proc. Natl Acad. Sci. USA 110, 15680-15685 (2013).
21. Zhang, J. et al. Real-space identification of intermolecular bonding with atomic force microscopy. Science 342, 611-614 (2013).
22. Aviram, A., Seiden, P. E. & Ratner, M. A. in Molecular Electronic Devices (ed. Carter, F. L.) 5-17 (Marcel Dekker, 1983).
23. Tylli, H. & Konschin, H. A Raman spectroscopic study of the OH and OD torsion in 1,2-dihydroxybenzene. J. Mol. Struct. 57, 13-19 (1979).
24. Navarrete, J. T. L. & Ramirez, F. J. A study by Raman spectroscopy and the semiempirical AM1 method on several 1,2-dihydroxybenzene solutions. Spectrochim Acta A 49, 1759-1767 (1993).
25. Hemraj-Benny, T. et al. Near-edge X-ray absorption fine structure spectroscopy as a tool for investigating nanomaterials. Small 2, 26-35 (2006).
26. Park, J. et al. Structural characterization of conjugated polyelectrolyte electron transport layers by NEXAFS spectroscopy. Adv. Mater. 20, 2491-2496 (2008).
27. Lee, D. W., Lim, C., Israelachvili, J. N. & Hwang, D. S. Strong adhesion and cohesion of chitosan in aqueous solutions. Langmuir 29, 14222-14229 (2013).
28. Anderson, T. H. et al. The contribution of DOPA to substratepeptide adhesion and internal cohesion of mussel-inspired synthetic peptide films. Adv. Funct. Mater. 20, 4196-4205 (2010).
29. Danner, E. W., Kan, Y. J., Hammer, M. U., Israelachvili, J. N. & Waite, J. H. Adhesion of mussel foot protein Mefp-5 to mica: An underwater superglue. Biochemistry 51, 6511-6518 (2012).
30. Wang, J. et al. Influence of binding-site density in wet bioadhesion. Adv. Mater. 20, 3872-3876 (2008).
31. Ahn, B. K., Kraft, S. & Sun, X. S. Chemical pathways of epoxidized and hydroxylated fatty acid methyl esters and triglycerides with phosphoric acid. J. Mater. Chem. 21, 9498-9505 (2011).
32. Ahn, B. K., Kraft, S., Wang, D. & Sun, X. S. Thermally stable, transparent, pressure-sensitive adhesives from epoxidized and dihydroxyl soybean oil. Biomacromolecules 12, 1839-1843 (2011).
33. Bunker, S. P. & Wool, R. P. Synthesis and characterization of monomers and polymers for adhesives from methyl oleate. J. Polym. Sci. Polym. Chem. 40, 451-458 (2002).
34. Israelachvili, J. et al. Recent advances in the surface forces apparatus (SFA) technique. Rep. Prog. Phys. 73, 036601 (2010).
35. Lee, D. W., Banquy, X. & Israelachvili, J. N. Stick-slip friction and wear of articular joints. Proc. Natl Acad. Sci. USA 110, E567-E574 (2013).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:
1. A monomer comprising the formula:
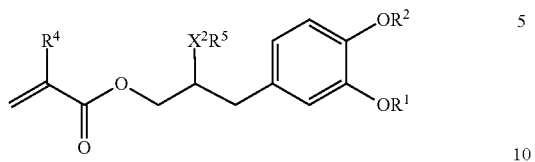
wherein:
each of $R^1$ and $R^2$, independently, is H, or alkyl;
$R^4$ is H or $C_1$-$C_6$ alkyl;
$R^5$ is H, or $C_1$-$C_6$ alkyl; and
$X^2$ is O or S.
* * * * *